US011279920B2

(12) United States Patent
Li et al.

(10) Patent No.: US 11,279,920 B2
(45) Date of Patent: *Mar. 22, 2022

(54) POLYPEPTIDES HAVING GLUCOAMYLASE ACTIVITY AND POLYNUCLEOTIDES ENCODING SAME

(71) Applicant: NOVOZYMES A/S, Bagsvaerd (DK)

(72) Inventors: Ming Li, Beijing (CN); Junxin Duan, Beijing (CN); Zheng Liu, Beijing (CN); Shiro Fukuyama, Narashino (JP); Keiichi Ayabe, Chiba-ken (JP); Guillermo Coward-Kelly, Wake Forest, NC (US); Randall Deinhammer, Wake Forest, NC (US)

(73) Assignee: NOVOZYMES A/S, Bagsvaerd (DK)

(*) Notice: Subject to any disclaimer, the term of this patent is extended or adjusted under 35 U.S.C. 154(b) by 0 days.

This patent is subject to a terminal disclaimer.

(21) Appl. No.: 16/135,370

(22) Filed: Sep. 19, 2018

(65) Prior Publication Data
US 2019/0002855 A1 Jan. 3, 2019

Related U.S. Application Data

(60) Continuation of application No. 15/443,931, filed on Feb. 27, 2017, now Pat. No. 10,196,620, which is a division of application No. 13/637,826, filed as application No. PCT/CN2011/072598 on Apr. 11, 2011, now Pat. No. 9,617,527.

(60) Provisional application No. 61/332,884, filed on May 10, 2010.

(30) Foreign Application Priority Data

Apr. 14, 2010 (WO) ................ PCT/CN2010/071753

(51) Int. Cl.
*C12N 9/34* (2006.01)
*C12P 7/08* (2006.01)
*C12P 19/02* (2006.01)

(52) U.S. Cl.
CPC ............ *C12N 9/2428* (2013.01); *C12P 19/02* (2013.01); *C12Y 302/01003* (2013.01); *Y02E 50/10* (2013.01)

(58) Field of Classification Search
None
See application file for complete search history.

(56) References Cited

U.S. PATENT DOCUMENTS

| 6,358,726 | B1 | 3/2002 | Takahura |
| 7,371,546 | B2 | 5/2008 | Svendsen |
| 7,541,026 | B2 | 6/2009 | Power |
| 8,343,747 | B2 | 1/2013 | Burke et al. |
| 9,617,527 | B2* | 4/2017 | Li ............... C12N 9/2428 |
| 10,196,620 | B2* | 2/2019 | Li ............... C12N 9/2428 |
| 2003/0027290 | A1 | 2/2003 | Nielsen |
| 2003/0082595 | A1 | 5/2003 | Jiang et al. |
| 2004/0115779 | A1 | 6/2004 | Olsen |
| 2005/0100996 | A1 | 5/2005 | Lantero |
| 2006/0270007 | A1 | 11/2006 | Nielsen |
| 2007/0184150 | A1 | 8/2007 | Bhargarva |
| 2008/0138871 | A1 | 6/2008 | Smith |
| 2009/0275080 | A1 | 11/2009 | Aehle et al. |
| 2010/0267114 | A1 | 10/2010 | Aehle et al. |
| 2013/0095522 | A1 | 4/2013 | Deinhammer et al. |
| 2014/0017749 | A1 | 1/2014 | Deinhammer et al. |

FOREIGN PATENT DOCUMENTS

| EP | 1916308 A1 | 4/2008 |
| WO | 92/02614 A1 | 2/1992 |
| WO | 99/19467 A1 | 4/1999 |
| WO | 00/075296 A1 | 12/2000 |
| WO | 2004/113551 A1 | 12/2004 |
| WO | 2005/113785 A2 | 12/2005 |
| WO | 2006/086792 A2 | 8/2006 |
| WO | 2009/100138 A2 | 8/2009 |
| WO | 2010/008841 A2 | 10/2010 |
| WO | 2011/100161 A1 | 8/2011 |
| WO | 2011/127802 A1 | 10/2011 |
| WO | 2012/109119 A2 | 8/2012 |
| WO | 2015/035914 A1 | 3/2015 |

OTHER PUBLICATIONS

Riaz et al, 2011, Food Chem., 130:24-30.*
Chou et al, 2006, Biochem., J., 396:469-477.*
Whisstock et al., 2003, Quarterly Reviews of Biophysics, 36:307-430.*
Guo et al, 2004, PNAS, 101:9205-9210.*
Takahashi et al, 1985, J. Biochem, 98:663-671.*
Devos et al., 2000, Proteins: Structure, Function, and Genetics, 41:98-107.*
Roth et al., 2018, Acta Cryst., D74: 463-470.*
Christiansen et al, 2009, FEBS Journal, 276:5005-5029.*
Kumar et al., 2009, Critical Reviews in Biotechnology, 29:225-255.*
Mahajan et al., Analytical Biochemistry, vol. 133, pp. 482-485 (1983).
Pandey, Starch, vol. 47, No. 11, pp. 439-445 (1995).
Peralta et al., Canadian Journal of Microbiology, vol. 44, No. 5, pp. 493-497 (1998).
Sasha et al., Starch, vol. 41, No. 2, pp. 57-64 (1989).

(Continued)

*Primary Examiner* — Jason Deveau Rosen

(74) *Attorney, Agent, or Firm* — David Fazzolare

(57) ABSTRACT

The present invention relates to isolated polypeptides having glucoamylase activity and isolated polynucleotides encoding the polypeptides. The invention also relates to nucleic acid constructs, vectors, and host cells comprising the polynucleotides as well as methods of producing and using the polypeptides.

28 Claims, 1 Drawing Sheet
Specification includes a Sequence Listing.

(56) References Cited

OTHER PUBLICATIONS

Yamasaki et al., Agricultural and Biological Chemistry, vol. 41, pp. 755-762 (1977).
Sun et al., 2007, W J Microbiol Bitechnol 23, 603-6.
Ben et al., 2001—Uniport Access No. Q9KWY6.
Chica et al., 2005, Curr Op Biotechnol 16(4), 378-384.
Sen et al., 2007, Appl Biochem Biotechnol 143(3), 212-223.
De Souza et al., 2010, Brazilian J Microbiol 41, 850-861.
Prakash 2010, Appl Biochem Biotechnol 160, 2401-2414.
Fukuda et al., 2009, Biochem Eng J 44, 2-12.
Sun et al., 2010, Appl Biochem Biotechnol 160, 988-1003.
Tawil et al., 2011, Biomacromolecules 12, 34-42.
Fedorova et al., 2007—Uniprot Access No. A1DJ85.
Yamasaki et al., 1977, Agric Biol Chem 41 (8), 1443-1450.
Riaz et al., 2011, Food Chem 130(1), 24-30.
Devos et al., 2000, Proteins Struc Func Bioinf 41, 98-107.
Da Silva et al., 1998, Can J Microbiol 44(5), 493-497.
Tian and Skolnick, J. Mol. Biol. (2003) 333, 863-882.
Addou et al., J. Mol. Biol. (2009) 387, 416-430.
Roth et al., Acta Cryst. (2018). D74, 463-470.
Esben Peter Friis Declaration under 37 CFR 1.132 dated Feb. 2021.

\* cited by examiner

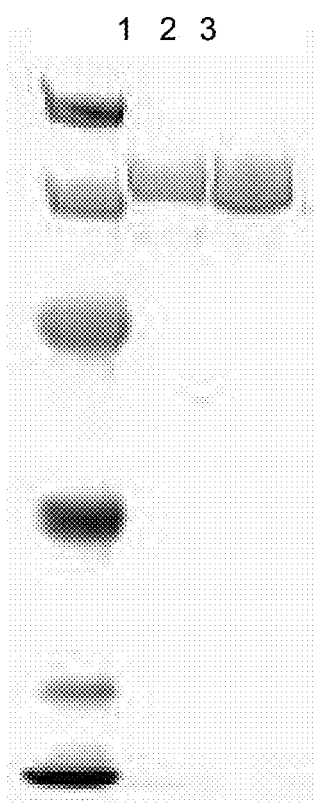

SEQUENCE LISTING

```
<160> NUMBER OF SEQ ID NOS: 9

<210> SEQ ID NO 1
<211> LENGTH: 1851
<212> TYPE: DNA
<213> ORGANISM: Penicillium oxalicum
<220> FEATURE:
<221> NAME/KEY: CDS
<222> LOCATION: (1)..(1851)

<400> SEQUENCE: 1 atg cgt ctc act cta tta tca ggt gta gcc ggc gtt ctc tgc gca gga      48
Met Arg Leu Thr Leu Leu Ser Gly Val Ala Gly Val Leu Cys Ala Gly
1               5                   10                  15 cag ctg acg gcg gcg cgt cct gat ccc aag ggt ggg aat ctg acg ccg      96
Gln Leu Thr Ala Ala Arg Pro Asp Pro Lys Gly Gly Asn Leu Thr Pro
            20                  25                  30 ttc atc cac aaa gag ggc gag cgg tcg ctc caa ggc atc ttg gac aat     144
Phe Ile His Lys Glu Gly Glu Arg Ser Leu Gln Gly Ile Leu Asp Asn
        35                  40                  45 ctc ggt ggg cga ggt aag aaa aca ccc ggc act gcc gca ggg ttg ttt     192
Leu Gly Gly Arg Gly Lys Lys Thr Pro Gly Thr Ala Ala Gly Leu Phe
    50                  55                  60 att gcc agt cca aac aca gag aat cca aac tat tat tat aca tgg act     240
Ile Ala Ser Pro Asn Thr Glu Asn Pro Asn Tyr Tyr Tyr Thr Trp Thr
65                  70                  75                  80 cgt gac tca gct ttg act gcc aag tgc ttg atc gac ctg ttc gaa gac     288
Arg Asp Ser Ala Leu Thr Ala Lys Cys Leu Ile Asp Leu Phe Glu Asp
                85                  90                  95 tct cgg gca aag ttt cca att gac cgc aaa tac ttg gaa aca gga att     336
Ser Arg Ala Lys Phe Pro Ile Asp Arg Lys Tyr Leu Glu Thr Gly Ile
            100                 105                 110 cgg gac tac gtg tcg tcc caa gca atc ctc cag agt gtg tct aat cct     384
Arg Asp Tyr Val Ser Ser Gln Ala Ile Leu Gln Ser Val Ser Asn Pro
        115                 120                 125
```

| | | |
|---|---|---|
| tct gga acc ctg aag gat ggc tct ggt ctg ggt gaa ccc aag ttt gag<br>Ser Gly Thr Leu Lys Asp Gly Ser Gly Leu Gly Glu Pro Lys Phe Glu<br>130                         135                     140 | 432 |
| att gac ctg aat ccc ttt tcg ggt gcc tgg ggt cgg cct cag cgg gat<br>Ile Asp Leu Asn Pro Phe Ser Gly Ala Trp Gly Arg Pro Gln Arg Asp<br>145                     150                     155                   160 | 480 |
| ggc cca gcg ctg cga gcg acc gct atg atc acc tac gcc aac tac ctg<br>Gly Pro Ala Leu Arg Ala Thr Ala Met Ile Thr Tyr Ala Asn Tyr Leu<br>                   165                     170                   175 | 528 |
| ata tcc cat ggt cag aaa tcg gat gtg tca cag gtc atg tgg ccg att<br>Ile Ser His Gly Gln Lys Ser Asp Val Ser Gln Val Met Trp Pro Ile<br>         180                     185                     190 | 576 |
| att gcc aat gat cta gca tat gtt ggt caa tac tgg aat aat acc gga<br>Ile Ala Asn Asp Leu Ala Tyr Val Gly Gln Tyr Trp Asn Asn Thr Gly<br>195                         200                     205 | 624 |
| ttt gac ctg tgg gaa gag gtg gat ggg tca agc ttt ttc acg att gcg<br>Phe Asp Leu Trp Glu Glu Val Asp Gly Ser Ser Phe Phe Thr Ile Ala<br>       210                     215                     220 | 672 |
| gtc cag cac cga gcc ctt gtt gaa ggc tcg caa ctg gcg aaa aag ctc<br>Val Gln His Arg Ala Leu Val Glu Gly Ser Gln Leu Ala Lys Lys Leu<br>225                       230                     235                   240 | 720 |
| ggc aag tcc tgc gat gcc tgt gat tct cag cct ccc cag ata ttg tgt<br>Gly Lys Ser Cys Asp Ala Cys Asp Ser Gln Pro Pro Gln Ile Leu Cys<br>                   245                     250                   255 | 768 |
| ttc ctg cag agt ttc tgg aac gga aag tac atc acc tcc aac atc aac<br>Phe Leu Gln Ser Phe Trp Asn Gly Lys Tyr Ile Thr Ser Asn Ile Asn<br>       260                     265                     270 | 816 |
| acg caa gca agc cgt tct ggt atc gac ctg gac tct gtc ctg gga agc<br>Thr Gln Ala Ser Arg Ser Gly Ile Asp Leu Asp Ser Val Leu Gly Ser<br>275                       280                     285 | 864 |
| att cat acc ttt gat ccc gaa gca gcc tgt gac gat gca act ttc cag<br>Ile His Thr Phe Asp Pro Glu Ala Ala Cys Asp Asp Ala Thr Phe Gln<br>         290                     295                     300 | 912 |
| cct tgt tct gcc cgc gct ctg gcg aac cac aag gtc tat gtg gat tcc<br>Pro Cys Ser Ala Arg Ala Leu Ala Asn His Lys Val Tyr Val Asp Ser<br>305                       310                     315                   320 | 960 |
| ttc cgc tct atc tac aag att aat gcg ggt ctt gca gag gga tcg gct<br>Phe Arg Ser Ile Tyr Lys Ile Asn Ala Gly Leu Ala Glu Gly Ser Ala<br>                   325                     330                   335 | 1008 |
| gcc aac gtt ggc cgc tac ccc gag gat gtt tac caa gga ggc aat cca<br>Ala Asn Val Gly Arg Tyr Pro Glu Asp Val Tyr Gln Gly Gly Asn Pro<br>               340                     345                     350 | 1056 |
| tgg tat ctc gcc acc cta ggc gca tct gaa ttg ctt tac gac gcc ttg<br>Trp Tyr Leu Ala Thr Leu Gly Ala Ser Glu Leu Leu Tyr Asp Ala Leu<br>             355                     360                     365 | 1104 |
| tac cag tgg gac aga ctt ggc aaa ctt gaa gtc tcg gag acc tcg ttg<br>Tyr Gln Trp Asp Arg Leu Gly Lys Leu Glu Val Ser Glu Thr Ser Leu<br>       370                     375                     380 | 1152 |
| tca ttc ttc aaa gac ttt gac gcg acc gtg aaa att ggc tcg tac tcg<br>Ser Phe Phe Lys Asp Phe Asp Ala Thr Val Lys Ile Gly Ser Tyr Ser<br>385                       390                     395                   400 | 1200 |
| agg aac agc aag acc tac aag aaa ttg acc cag tcc atc aag tcg tac<br>Arg Asn Ser Lys Thr Tyr Lys Lys Leu Thr Gln Ser Ile Lys Ser Tyr<br>                   405                     410                   415 | 1248 |
| gcg gac ggg ttc atc cag tta gtg cag cag tac act cct tct aat gga<br>Ala Asp Gly Phe Ile Gln Leu Val Gln Gln Tyr Thr Pro Ser Asn Gly<br>               420                     425                     430 | 1296 |
| tct ctg gcc gag caa tac gat cgc aat acg gct gct cct ctc tct gca<br>Ser Leu Ala Glu Gln Tyr Asp Arg Asn Thr Ala Ala Pro Leu Ser Ala | 1344 |

```
                435                 440                 445
aac gat ctg act tgg tca ttt gcc tct ttc ttg acg gct acg caa cgc      1392
Asn Asp Leu Thr Trp Ser Phe Ala Ser Phe Leu Thr Ala Thr Gln Arg
    450                 455                 460 cgc gat gcc gtg gtt cct ccc tcc tgg ggc gca aag tcg gca aac aaa      1440
Arg Asp Ala Val Val Pro Pro Ser Trp Gly Ala Lys Ser Ala Asn Lys
465                 470                 475                 480 gtc cca acc act tgt tca gcc tcc cct gtt gtg ggt act tat aag gcg      1488
Val Pro Thr Thr Cys Ser Ala Ser Pro Val Val Gly Thr Tyr Lys Ala
                485                 490                 495 ccc acg gca act ttc tca tcc aag act aag tgc gtc ccc gct aaa gat      1536
Pro Thr Ala Thr Phe Ser Ser Lys Thr Lys Cys Val Pro Ala Lys Asp
            500                 505                 510 att gtg cct atc acg ttc tac ctg att gag aac act tac tat gga gag      1584
Ile Val Pro Ile Thr Phe Tyr Leu Ile Glu Asn Thr Tyr Tyr Gly Glu
            515                 520                 525 aac gtc ttc atg agt ggc aac att act gcg ctg ggt aac tgg gac gcc      1632
Asn Val Phe Met Ser Gly Asn Ile Thr Ala Leu Gly Asn Trp Asp Ala
    530                 535                 540 aag aaa ggc ttc cca ctc acc gca aac ctc tac acg caa gat caa aac      1680
Lys Lys Gly Phe Pro Leu Thr Ala Asn Leu Tyr Thr Gln Asp Gln Asn
545                 550                 555                 560 ttg tgg ttc gcc agt gtc gag ttc atc cca gca ggc aca ccc ttt gag      1728
Leu Trp Phe Ala Ser Val Glu Phe Ile Pro Ala Gly Thr Pro Phe Glu
                565                 570                 575 tac aag tac tac aag gtc gag ccc aat ggc gat att act tgg gag aag      1776
Tyr Lys Tyr Tyr Lys Val Glu Pro Asn Gly Asp Ile Thr Trp Glu Lys
                580                 585                 590 ggt ccc aac cgg gtg ttc gtc gct ccc acg gga tgc cca gtt cag cct      1824
Gly Pro Asn Arg Val Phe Val Ala Pro Thr Gly Cys Pro Val Gln Pro
            595                 600                 605 cac tcc aac gac gtg tgg cag ttt tga                                  1851
His Ser Asn Asp Val Trp Gln Phe
    610                 615

<210> SEQ ID NO 2
<211> LENGTH: 616
<212> TYPE: PRT
<213> ORGANISM: Penicillium oxalicum

<400> SEQUENCE: 2

Met Arg Leu Thr Leu Leu Ser Gly Val Ala Gly Val Leu Cys Ala Gly
1               5                   10                  15

Gln Leu Thr Ala Ala Arg Pro Asp Pro Lys Gly Gly Asn Leu Thr Pro
            20                  25                  30

Phe Ile His Lys Glu Gly Glu Arg Ser Leu Gln Gly Ile Leu Asp Asn
        35                  40                  45

Leu Gly Gly Arg Gly Lys Lys Thr Pro Gly Thr Ala Ala Gly Leu Phe
    50                  55                  60

Ile Ala Ser Pro Asn Thr Glu Asn Pro Asn Tyr Tyr Tyr Thr Trp Thr
65                  70                  75                  80

Arg Asp Ser Ala Leu Thr Ala Lys Cys Leu Ile Asp Leu Phe Glu Asp
                85                  90                  95

Ser Arg Ala Lys Phe Pro Ile Asp Arg Lys Tyr Leu Glu Thr Gly Ile
            100                 105                 110

Arg Asp Tyr Val Ser Ser Gln Ala Ile Leu Gln Ser Val Ser Asn Pro
        115                 120                 125

Ser Gly Thr Leu Lys Asp Gly Ser Gly Leu Gly Glu Pro Lys Phe Glu
```

```
            130                 135                 140
Ile Asp Leu Asn Pro Phe Ser Gly Ala Trp Gly Arg Pro Gln Arg Asp
145                 150                 155                 160

Gly Pro Ala Leu Arg Ala Thr Ala Met Ile Thr Tyr Ala Asn Tyr Leu
                    165                 170                 175

Ile Ser His Gly Gln Lys Ser Asp Val Ser Gln Val Met Trp Pro Ile
                180                 185                 190

Ile Ala Asn Asp Leu Ala Tyr Val Gly Gln Tyr Trp Asn Asn Thr Gly
                195                 200                 205

Phe Asp Leu Trp Glu Glu Val Asp Gly Ser Ser Phe Phe Thr Ile Ala
            210                 215                 220

Val Gln His Arg Ala Leu Val Glu Gly Ser Gln Leu Ala Lys Lys Leu
225                 230                 235                 240

Gly Lys Ser Cys Asp Ala Cys Asp Ser Gln Pro Pro Gln Ile Leu Cys
                    245                 250                 255

Phe Leu Gln Ser Phe Trp Asn Gly Lys Tyr Ile Thr Ser Asn Ile Asn
                260                 265                 270

Thr Gln Ala Ser Arg Ser Gly Ile Asp Leu Asp Ser Val Leu Gly Ser
                275                 280                 285

Ile His Thr Phe Asp Pro Glu Ala Ala Cys Asp Asp Ala Thr Phe Gln
            290                 295                 300

Pro Cys Ser Ala Arg Ala Leu Ala Asn His Lys Val Tyr Val Asp Ser
305                 310                 315                 320

Phe Arg Ser Ile Tyr Lys Ile Asn Ala Gly Leu Ala Glu Gly Ser Ala
                    325                 330                 335

Ala Asn Val Gly Arg Tyr Pro Glu Asp Val Tyr Gln Gly Gly Asn Pro
                340                 345                 350

Trp Tyr Leu Ala Thr Leu Gly Ala Ser Glu Leu Leu Tyr Asp Ala Leu
                355                 360                 365

Tyr Gln Trp Asp Arg Leu Gly Lys Leu Glu Val Ser Glu Thr Ser Leu
            370                 375                 380

Ser Phe Phe Lys Asp Phe Asp Ala Thr Val Lys Ile Gly Ser Tyr Ser
385                 390                 395                 400

Arg Asn Ser Lys Thr Tyr Lys Lys Leu Thr Gln Ser Ile Lys Ser Tyr
                    405                 410                 415

Ala Asp Gly Phe Ile Gln Leu Val Gln Gln Tyr Thr Pro Ser Asn Gly
                420                 425                 430

Ser Leu Ala Glu Gln Tyr Asp Arg Asn Thr Ala Ala Pro Leu Ser Ala
                435                 440                 445

Asn Asp Leu Thr Trp Ser Phe Ala Ser Phe Leu Thr Ala Thr Gln Arg
            450                 455                 460

Arg Asp Ala Val Val Pro Pro Ser Trp Gly Lys Ser Ala Asn Lys
465                 470                 475                 480

Val Pro Thr Thr Cys Ser Ala Ser Pro Val Val Gly Thr Tyr Lys Ala
                    485                 490                 495

Pro Thr Ala Thr Phe Ser Ser Lys Thr Lys Cys Val Pro Ala Lys Asp
                500                 505                 510

Ile Val Pro Ile Thr Phe Tyr Leu Ile Glu Asn Thr Tyr Tyr Gly Glu
                515                 520                 525

Asn Val Phe Met Ser Gly Asn Ile Thr Ala Leu Gly Asn Trp Asp Ala
            530                 535                 540

Lys Lys Gly Phe Pro Leu Thr Ala Asn Leu Tyr Thr Gln Asp Gln Asn
545                 550                 555                 560
```

```
Leu Trp Phe Ala Ser Val Glu Phe Ile Pro Ala Gly Thr Pro Phe Glu
            565                 570                 575

Tyr Lys Tyr Tyr Lys Val Glu Pro Asn Gly Asp Ile Thr Trp Glu Lys
            580                 585                 590

Gly Pro Asn Arg Val Phe Val Ala Pro Thr Gly Cys Pro Val Gln Pro
            595                 600                 605

His Ser Asn Asp Val Trp Gln Phe
    610                 615

<210> SEQ ID NO 3
<211> LENGTH: 34
<212> TYPE: DNA
<213> ORGANISM: Artificial Sequence
<220> FEATURE:
<223> OTHER INFORMATION: primer

<400> SEQUENCE: 3
tcgcgatccg ttttcgcatt tatcgtgaaa cgct                           34

<210> SEQ ID NO 4
<211> LENGTH: 33
<212> TYPE: DNA
<213> ORGANISM: Artificial Sequence
<220> FEATURE:
<223> OTHER INFORMATION: primer

<400> SEQUENCE: 4
ccgcaaacgc tggtgaaagt aaaagatgct gaa                            33

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
agcgtttgcg gccgcgatcc                                           20

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
ttattcggtc gaaaaggatc c                                         21

<210> SEQ ID NO 7
<211> LENGTH: 25
<212> TYPE: DNA
<213> ORGANISM: Artificial Sequence
<220> FEATURE:
<223> OTHER INFORMATION: primer

<400> SEQUENCE: 7
atgcgtctca ctctattatc aggtg                                     25

<210> SEQ ID NO 8
<211> LENGTH: 39
<212> TYPE: DNA
<213> ORGANISM: Artificial Sequence
<220> FEATURE:
```

```
<223> OTHER INFORMATION: primer

<400> SEQUENCE: 8
acacaactgg ggatccacca tgcgtctcac tctattatc                    39

<210> SEQ ID NO 9
<211> LENGTH: 37
<212> TYPE: DNA
<213> ORGANISM: Artificial Sequence
<220> FEATURE:
<223> OTHER INFORMATION: primer

<400> SEQUENCE: 9
agatctcgag aagcttaaaa ctgccacacg tcgttgg                      37
```

POLYPEPTIDES HAVING GLUCOAMYLASE ACTIVITY AND POLYNUCLEOTIDES ENCODING SAME

CROSS-REFERENCE TO RELATED APPLICATIONS

This application is a continuation of U.S. application Ser. No. 15/443,931 filed Feb. 27, 2017, now U.S. Pat. No. 10,196,620, which is a divisional application of U.S. application Ser. No. 13/637,826, filed Sep. 27, 2012, now U.S. Pat. No. 9,617,527, which is a 35 U.S.C. § 371 national application of PCT/CN2011/072598 filed Apr. 11, 2011, which claims the benefit of U.S. Provisional Application Ser. No. 61/332,884, filed May 5, 2010, and PCT/CN2010/071753 filed Apr. 14, 2010. The contents of these applications are fullly incorporated herein by reference.

REFERENCE TO A SEQUENCE LISTING

This application contains a Sequence Listing in computer readable form. The computer readable form is incorporated herein by reference.

REFERENCE TO A DEPOSIT OF BIOLOGICAL MATERIAL

This application contains a reference to a deposit of biological material, which deposit is incorporated herein by reference. For complete information see "Deposit of Biological Material"—section of the description.

BACKGROUND OF THE INVENTION

Field of the Invention

The present invention relates to isolated polypeptides having glucoamylase activity and isolated polynucleotides encoding the polypeptides. The invention also relates to nucleic acid constructs, vectors, and host cells comprising the polynucleotides as well as methods for producing and using the polypeptides, and to uses of glucoamylases of the invention and a process for producing a liquefaction, saccharification and/or fermentation product using the glucoamylase of the present invention. The present invention also relates to a composition comprising a glucoamylase of the invention.

Description of the Related Art

Glucoamylase (1,4-alpha-D-glucan glucohydrolase, EC 3.2.1.3) is an enzyme, which catalyzes the release of D-glucose from the non-reducing ends of starch or related oligo- and poly-saccharide molecules. Glucoamylases are produced by several filamentous fungi and yeast, with those from *Aspergillus* being commercially most important.

Glucoamylases (equivalent to amyloglucosidase, AMG) are mostly sold as saccharification enzymes to various industries including brewing, starch and fuels. In starch and fuel industries, glucoamylases are commercially used to convert starchy material, which is already partially hydrolyzed by an alpha-amylase, to glucose. The glucose may then be converted directly or indirectly into a fermentation product using a fermenting organism. Examples of commercial fermentation products include alcohols (e.g., ethanol, methanol, butanol, 1,3-propanediol); organic acids (e.g., citric acid, acetic acid, itaconic acid, lactic acid, gluconic acid, gluconate, lactic acid, succinic acid, 2,5-diketo-D-gluconic acid); ketones (e.g., acetone); amino acids (e.g., glutamic acid); gases (e.g., $H_2$ and $CO_2$), and more complex compounds, including, for example, antibiotics (e.g., penicillin and tetracycline); enzymes; vitamins (e.g., riboflavin, $B_{12}$, beta-carotene); hormones, and other compounds which are difficult to produce synthetically. Fermentation processes are also commonly used in the consumable alcohol (e.g., beer and wine), dairy (e.g., in the production of yogurt and cheese), leather, beverage and tobacco industries.

The end product may also be syrup. For instance, the end product may be glucose, but may also be converted, e.g., by glucose isomerase to fructose or a mixture composed almost equally of glucose and fructose. This mixture, or a mixture further enriched with fructose, is the most commonly used high fructose corn syrup (HFCS) commercialized throughout the world.

The purification and properties of two forms of glucoamylase from *Penicillium oxalicum* were disclosed (Yoshiki YAMASAKI, Agric. Biol. Chem., 41 (5), 755-762, 1977). Both glucoamylases were stable at up to 55° C., but at temperature around 60° C., the glucoamylase activities dropped sharply. The sequences of the two forms of glucoamylases were not disclosed in this article or even later publications.

SUMMARY OF THE INVENTION

The present invention relates to an isolated polypeptide having glucoamylase activity, selected from the group consisting of:

(a) a polypeptide comprising an amino acid sequence having preferably at least 61.5%, more preferably at least 63%, more preferably at least 65%, more preferably at least 68%, more preferably at least 70%, more preferably at least 75%, more preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, 97%, 98%, 99% or 100% identity to the mature polypeptide of SEQ ID NO: 2;

(b) a polypeptide encoded by a polynucleotide that hybridizes under preferably at least low stringency conditions, more preferably at least medium stringency conditions, even more preferably at least medium-high stringency conditions, most preferably at least high stringency, and even most preferably at least very high stringency conditions with (i) the mature polypeptide coding sequence of SEQ ID NO: 1, (ii) the genomic DNA sequence comprising the mature polypeptide coding sequence of SEQ ID NO: 1, or (iii) a full-length complementary strand of (i) or (ii);

(c) a polypeptide encoded by a polynucleotide comprising a nucleotide sequence having at least 61.5%, more preferably at least 63%, more preferably at least 65%, more preferably at least 68%, more preferably at least 70%, more preferably at least 75%, more preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, 97%, 98%, 99% or 100% identity to the mature polypeptide coding sequence of SEQ ID NO: 1;

(d) a variant comprising a substitution, deletion, and/or insertion of one or more (e.g., several) amino acids of the mature polypeptide of SEQ ID NO: 2; and (e) a fragment of a polypeptide of (a), (b),(c) or (d) that has glucoamylase activity.

The present invention also relates to isolated polynucleotides comprising the nucleotide sequence that encodes a polypeptide of the present invention.

The present invention also relates to nucleic acid constructs, recombinant expression vectors, and recombinant host cells comprising the polynucleotides, and to methods of producing the polypeptides having glucoamylase activity.

The present invention also relates to transgenic plants, plant parts or plant cells transformed with a polynucleotide of the present invention.

The present invention also relates to compositions comprising the polypeptide of present invention.

The present invention also relates to use of the polypeptides of the present invention for liquefaction, saccharification and/or fermentation process, preferably in starch conversion; to use of the polypeptides of the present invention for production of syrup, beverage and/or a fermentation product; and to use of the polypeptides of the present invention for brewing.

The present invention also relates to a process for producing a liquefaction, saccharification and/or fermentation product from starch-containing material comprising the step of:

treating starch-containing material with the polypeptides of the present invention.

BRIEF DESCRIPTION OF THE FIGURES

FIG. 1 shows the SDS-PAGE electrophoresis of the purified *Penicillium oxalicum* glucoamylase sample of the present invention. Lane 1: Marker (97, 66, 45, 30, 20.1 and 14.4 kDa); Lane 2: the supernatant of *Penicillium oxalicum* glucoamylase of the present invention before purification; Lane 3: *Penicillium oxalicum* glucoamylase of the present invention.

Polynucleotide sequence and the deduced amino acid sequence of the *Penicillium oxalicum* glucoamylase of the present invention are shown in SEQ ID NOs: 1 and 2, respectively.

DESCRIPTION OF THE INVENTION

It is an object of the present invention to provide polypeptides having glucoamylase activity and polynucleotides encoding the polypeptides, preferably, to provide polypeptides having glucoamylase activity and polynucleotides encoding the polypeptides with highly thermostability.

Definitions

Glucoamylase activity: The term "glucoamylase (1,4-alpha-D-glucan glucohydrolase, EC 3.2.1.3) activity" is defined herein as an enzyme activity, which catalyzes the release of D-glucose from the non-reducing ends of starch or related oligo- and poly-saccharide molecules. Glucoamylase activity may be measured in AGU units. See the "Glucoamylase activity"—section below in the "Materials and Methods" section.

The polypeptides of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the glucoamylase activity of the mature polypeptide of SEQ ID NO: 2.

Isolated polypeptide: The terms "isolated" and "purified" mean a polypeptide or polynucleotide that is removed from at least one component with which it is naturally associated. For example, a polypeptide may be at least 1% pure, e.g., at least 5% pure, at least 10% pure, at least 20% pure, at least 40% pure, at least 60% pure, at least 80% pure, and at least 90% pure, as determined by SDS-PAGE and a polynucleotide may be at least 1% pure, e.g., at least 5% pure, at least 10% pure, at least 20% pure, at least 40% pure, at least 60% pure, at least 80% pure, at least 90% pure, and at least 95% pure, as determined by agarose electrophoresis.

Mature polypeptide: The term "mature polypeptide" is defined herein as a polypeptide in its final form following translation and any post-translational modifications, such as N-terminal processing, C-terminal truncation, glycosylation, phosphorylation, etc. In one aspect, the mature polypeptide is amino acids 22 to 616 of SEQ ID NO: 2 based on the SignalP (Nielsen et al., 1997, *Protein Engineering* 10: 1-6) program that predicts amino acids 1 to 21 of SEQ ID NO: 2 are a signal peptide.

Mature polypeptide coding sequence: The term "mature polypeptide coding sequence" is defined herein as a nucleotide sequence that encodes a mature polypeptide having glucoamylase activity. In one aspect, the mature polypeptide coding sequence is nucleotides 64 to 1848 of SEQ ID NO: 1 based on SignalP (Nielsen et al., 1997, supra) program that predicts nucleotides 1 to 63 of SEQ ID NO: 1 encode a signal peptide.

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

A polypeptide having glucoamylase activity (uniprot: P69328) from *Aspergillus niger* (Svensson, B. Larsen, K. Gunnarsson, A.; "Characterization of a glucoamylase G2 from *Aspergillus niger*."; Eur. J. Biochem. 154:497-502

(1986)) is 48.1% identical to the *Penicillium oxalicum* glucoamylase of SEQ ID NO: 2 of the present invention.

A polypeptide having glucoamylase activity (UNIPROT: Q03045) from *Hormoconis resinae* (Joutsjoki, V. V. Torkkeli, T. K.; "Glucoamylase P gene of *Hormoconis resinae*: molecular cloning, sequencing and introduction into *Trichoderma reesei*."; FEMS Microbiol. Lett. 78:237-243 (1992)) is 51.68% (gapless) identical to the *Penicillium oxalicum* glucoamylase of SEQ ID NO: 2 of the present invention.

Homologous sequence: The term "homologous sequence" is defined herein as a predicted protein having an E value (or expectancy score) of less than 0.001 in a tfasty search (Pearson, W. R., 1999, in *Bioinformatics Methods and Protocols*, S. Misener and S. A. Krawetz, ed., pp. 185-219) with the *Penicillium oxalicum* [*E. coli* DSM 23123] glucoamylase of SEQ ID NO: 2 or the mature polypeptide thereof.

Polypeptide fragment: The term "polypeptide fragment" is defined herein as a polypeptide having one or more (e.g., several) amino acids deleted from the amino and/or carboxyl terminus of the mature polypeptide of SEQ ID NO: 2; or a homologous sequence thereof; wherein the fragment has glucoamylase activity. In one aspect, a fragment contains at least 473 amino acid residues, e.g., amino acids 28 to 500 of SEQ ID NO: 2 (GH15_1 domain of the present invention), more preferably at least 575 amino acid residues, e.g., amino acids 28 to 500 (GH15_1 domain of the present invention) and amino acids 514 to 615 of SEQ ID NO: 2 (CBM20_x domain of the present invention), or a homologous sequence thereof.

Subsequence: The term "subsequence" is defined herein as a nucleotide sequence having one or more (e.g., several) nucleotides deleted from the 5' and/or 3' end of the mature polypeptide coding sequence of SEQ ID NO: 1; or a homologous sequence thereof; wherein the subsequence encodes a polypeptide fragment having glucoamylase activity. In one aspect, a subsequence contains at least 1419 nucleotides, for example, the nucleotides encoding GH15_1 domain (nucleotides 82-1500) of the present invention; more preferably at least 1725 nucleotides for example, the nucleotides encoding GH15_1 domain and CBM20_x (nucleotides 1540-1845) of the present invention, of the mature polypeptide coding sequence of SEQ ID NO: 1 or a homologous sequence thereof.

Allelic variant: The term "allelic variant" denotes herein any of two or more (e.g., several) alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide that is isolated from a source. In a preferred aspect, the polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99% pure, and even most preferably at least 99.5% pure by weight. The polynucleotides of the present invention are preferably in a substantially pure form, i.e., that the polynucleotide preparation is essentially free of other polynucleotide material with which it is natively or recombinantly associated. The polynucleotides may be of genomic, cDNA, RNA, semisynthetic, synthetic origin, or any combinations thereof.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant nucleotide sequence.

cDNA: The term "cDNA" is defined herein as a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded isolated from a naturally occurring gene, which is modified to contain segments of nucleic acids in a manner that would not otherwise exist in nature. The nucleic acid construct can be also synthetic. The term nucleic acid construct is synonymous with the term "expression cassette" when the nucleic acid construct contains the control sequences required for expression of a coding sequence of the present invention.

Control sequences: The term "control sequences" is defined herein to include all components necessary for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of a polynucleotide sequence such that the control sequence directs the expression of the coding sequence of a polypeptide.

Expression: The term "expression" includes any step involved in the production of a polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the present invention and is operably linked to additional nucleotides that provide for its expression.

Host cell: The term "host cell", as used herein, includes any cell type that is susceptible to transformation, transfection, transduction, and the like with a nucleic acid construct or expression vector comprising a polynucleotide of the present invention.

Modification: The term "modification" means herein any chemical modification of the polypeptide comprising or consisting of the mature polypeptide of SEQ ID NO: 2; or a homologous sequence thereof; as well as genetic manipulation of the DNA encoding such a polypeptide. The modification can be a substitution, a deletion and/or an insertion of one or more (e.g., several) amino acids as well as replacements of one or more (e.g., several) amino acid side chains.

Artificial variant: When used herein, the term "artificial variant" means a polypeptide having glucoamylase activity produced by an organism expressing a modified polynucleotide sequence of the mature polypeptide coding sequence of SEQ ID NO: 1; or a homologous sequence thereof. The modified nucleotide sequence is obtained through human intervention by modification of the polynucleotide sequence disclosed in SEQ ID NO: 1; or a homologous sequence thereof.

Polypeptides Having Glucoamylase Activity

In a first aspect, the present invention relates to isolated polypeptides comprising amino acid sequences having a degree of sequence identity to the mature polypeptide of SEQ ID NO: 2 of preferably at least 61.5%, more preferably at least 63%, more preferably at least 65%, more preferably at least 68%, more preferably at least 70%, more preferably at least 75%, more preferably at least 80%, more preferably at least 85%, even more preferably at least 90%, most preferably at least 95%, and even most preferably at least 96%, at least 97%, at least 98%, at least 99%, or at least 100%, which have glucoamylase activity (hereinafter "homologous polypeptides"). In a preferred aspect, the homologous polypeptides comprise amino acid sequences that differ by ten amino acids, preferably by nine amino acids, preferably by eight amino acids, preferably by seven amino acids, preferably by six amino acids, preferably by five amino acids, more preferably by four amino acids, even more preferably by three amino acids, most preferably by two amino acids, and even most preferably by one amino acid from the mature polypeptide of SEQ ID NO: 2.

A polypeptide of the present invention preferably comprises the amino acid sequence of SEQ ID NO: 2, an allelic variant thereof. In a preferred aspect, a polypeptide of the present invention comprises the amino acid sequence of SEQ ID NO: 2; or a fragment thereof having glucoamylase activity. In another preferred aspect, the polypeptide comprises the mature polypeptide of SEQ ID NO: 2. In another preferred aspect, a polypeptide of the present invention comprises amino acids 22 to 616 of SEQ ID NO: 2, or an allelic variant thereof; or a fragment thereof having glucoamylase activity. In another preferred aspect, the polypeptide consists of the amino acid sequence of SEQ ID NO: 2 or an allelic variant thereof; or a fragment thereof having glucoamylase activity. In another preferred aspect, the polypeptide consists of the amino acid sequence of SEQ ID NO: 2. In another preferred aspect, the polypeptide consists of the mature polypeptide of SEQ ID NO: 2. In another preferred aspect, the polypeptide consists of amino acids 22 to 616 of SEQ ID NO: 2 or an allelic variant thereof; or a fragment thereof having glucoamylase activity. In another preferred aspect, the polypeptide consists of amino acids 22 to 616 of SEQ ID NO: 2. In a preferred aspect, the mature polypeptide is amino acids 22 to 616 of SEQ ID NO: 2.

In a second aspect, the present invention relates to isolated polypeptides having glucoamylase activity that are encoded by polynucleotides that hybridize under preferably very low stringency conditions, more preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, (ii) the genomic DNA sequence comprising the mature polypeptide coding sequence of SEQ ID NO: 1, or (iii) a full-length complementary strand of (i) or (ii) (J. Sambrook, E. F. Fritsch, and T. Maniatis, 1989, *Molecular Cloning, A Laboratory Manual*, 2d edition, Cold Spring Harbor, N.Y.).

The nucleotide sequence of SEQ ID NO: 1; or a subsequence thereof; as well as the amino acid sequence of SEQ ID NO: 2; or a fragment thereof; may be used to design nucleic acid probes to identify and clone DNA encoding polypeptides having glucoamylase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes that are preferably at least 600 nucleotides, more preferably at least 800 nucleotides, even more preferably at least 1000 nucleotides, even more preferably at least 1500 nucleotides, or most preferably at least 1800 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may, therefore, be screened for DNA that hybridizes with the probes described above and encodes a polypeptide having glucoamylase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1, or a subsequence thereof, the carrier material is preferably used in a Southern blot.

For purposes of the present invention, hybridization indicates that the nucleotide sequence hybridizes to a labeled nucleic acid probe corresponding to the mature polypeptide coding sequence of SEQ ID NO: 1; the genomic DNA sequence comprising the mature polypeptide coding sequence of SEQ ID NO: 1; its full-length complementary strand; or a subsequence thereof; under very low to very high stringency conditions. Molecules to which the nucleic acid probe hybridizes under these conditions can be detected using, for example, X-ray film.

In a preferred aspect, the nucleic acid probe is the mature polypeptide coding sequence of SEQ ID NO: 1. In another preferred aspect, the nucleic acid probe is nucleotides 64 to 1848 of SEQ ID NO: 1. In another preferred aspect, the nucleic acid probe is a polynucleotide sequence that encodes the polypeptide of SEQ ID NO: 2, or a subsequence thereof. In another preferred aspect, the nucleic acid probe is SEQ ID NO: 1. In another preferred aspect, the nucleic acid probe is the polynucleotide sequence contained in plasmid AMG 1 which is contained in E. coli DSM 23123, wherein the polynucleotide sequence thereof encodes a polypeptide having glucoamylase activity. In another preferred aspect, the nucleic acid probe is the mature polypeptide coding region contained in plasmid AMG 1 which is contained in E. coli DSM 23123. In another preferred aspect, the nucleic acid probe is nucleotides 82 to 1500, nucleotides 1504 to 1845, of SEQ ID NO: 1.

For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at 45° C. (very low stringency), more preferably at 50° C. (low stringency), more preferably at 55° C. (medium stringency), more preferably at 60° C. (medium-high stringency), even more preferably at 65° C. (high stringency), and most preferably at 70° C. (very high stringency).

For short probes of about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1× Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes of about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third aspect, the present invention relates to isolated polypeptides having glucoamylase activity encoded by polynucleotides comprising or consisting of nucleotide sequences having a degree of sequence identity to the mature polypeptide coding sequence of SEQ ID NO: 1 of preferably at least 61.5%, more preferably at least 63%, more preferably at least 65%, more preferably at least 68%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which encode a polypeptide having glucoamylase activity. See "polynucleotide"—section herein.

In a fourth aspect, the present invention relates to artificial variants comprising a substitution, deletion, and/or insertion of one or more (e.g., several) amino acids of the mature polypeptide of SEQ ID NO: 2, or a homologous sequence thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., glucoamylase activity) to identify amino acid residues that are critical to the activity of the molecule. See also, Hilton et al., 1996,

*J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to a polypeptide according to the invention.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The amino acid substitutions, deletions and/or insertions of the mature polypeptide of SEQ ID NO: 2 can be at most 10, preferably at most 9, more preferably at most 8, more preferably at most 7, more preferably at most 6, more preferably at most 5, more preferably at most 4, even more preferably at most 3, most preferably at most 2, and even most preferably at most 1.

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

A fusion polypeptide can further comprise a cleavage site. Upon secretion of the fusion protein, the site is cleaved releasing the polypeptide having glucoamylase activity from the fusion protein. Examples of cleavage sites include, but are not limited to, a Kex2 site that encodes the dipeptide Lys-Arg (Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381), an Ile-(Glu or Asp)-Gly-Arg site, which is cleaved by a Factor Xa protease after the arginine residue (Eaton et al., 1986, *Biochem.* 25: 505-512); a Asp-Asp-Asp-Asp-Lys site, which is cleaved by an enterokinase after the lysine (Collins-Racie et al., 1995, *Biotechnology* 13: 982-987); a His-Tyr-Glu site or His-Tyr-Asp site, which is cleaved by Genenase I (Carter et al., 1989, *Proteins: Structure, Function, and Genetics* 6: 240-248); a Leu-Val-Pro-Arg-Gly-Ser site, which is cleaved by thrombin after the Arg (Stevens, 2003, *Drug Discovery World* 4: 35-48); a Glu-Asn-Leu-Tyr-Phe-Gln-Gly site, which is cleaved by TEV protease after the Gln (Stevens, 2003, supra); and a Leu-Glu-Val-Leu-Phe-Gln-Gly-Pro site, which is cleaved by a genetically engineered form of human rhinovirus 3C protease after the Gln (Stevens, 2003, supra).

In a preferred aspect, a polypeptide of the present invention is encoded by a polynucleotide comprising or consisting of the nucleotide sequence of SEQ ID NO: 1; or a subsequence thereof encoding a fragment having glucoamylase activity.

In a preferred aspect, a polypeptide of the present invention is encoded by a polynucleotide comprising or consisting of the mature polypeptide coding sequence of SEQ ID NO: 1.

In a preferred aspect, a polypeptide of the present invention is encoded by the polynucleotide contained in plasmid AMG 1 which is contained in *E. coli* DSM 23123.

In a preferred aspect, the mature polypeptide coding sequence is nucleotides 64 to 1848 of SEQ ID NO: 1.

Sources of Polypeptides Having Glucoamylase Activity

A polypeptide having glucoamylase activity of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide having glucoamylase activity of the present invention may be a fungal polypeptide. For example, the polypeptide may be a yeast polypeptide such as a *Candida, Kluyveromyces, Pichia, Saccharomyces, Schizosaccharomyces,* or *Yarrowia* polypeptide having glucoamylase activity; or more preferably a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* polypeptide having glucoamylase activity.

In another preferred aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum,*

*Fusarium reticulatum, Fusarium roseum, Fusarium sambucinum, Fusarium sarcochroum, Fusarium sporotrichioides, Fusarium suiphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Penicillium thomii, Penicillium oxalicum, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei,* or *Trichoderma viride* polypeptide having glucoamylase activity.

In a more preferred aspect, the polypeptide is a *Penicillium oxalicum* polypeptide having glucoamylase activity. In a most preferred aspect, the polypeptide is a *Penicillium oxalicum* polypeptide having glucoamylase activity, e.g., the polypeptide comprising the mature polypeptide of SEQ ID NO: 2.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide encoding a polypeptide has been detected with the probe(s), the polynucleotide can be isolated or cloned by utilizing techniques that are well known to those of ordinary skill in the art (see, e.g., Sambrook et al., 1989, supra).

Polynucleotides

The present invention also relates to isolated polynucleotides comprising or consisting of nucleotide sequences that encode polypeptides having glucoamylase activity of the present invention.

In a preferred aspect, a nucleotide sequence of the present invention comprises or consists of SEQ ID NO: 1. In another more preferred aspect, the nucleotide sequence comprises or consists of the polynucleotide sequence contained in plasmid AMG 1 which is contained in *E. coli* DSM 23123. In another preferred aspect, the nucleotide sequence comprises or consists of the mature polypeptide coding sequence of SEQ ID NO: 1. In another preferred aspect, mature polypeptide coding sequence is nucleotides 64 to 1848 of SEQ ID NO: 1. In another more preferred aspect, the nucleotide sequence comprises or consists of the mature polypeptide coding sequence contained in plasmid AMG 1 which is contained in *E. coli* DSM 23123. The present invention also encompasses nucleotide sequences that encode polypeptides comprising or consisting of the amino acid sequence of SEQ ID NO: 2 or the mature polypeptide thereof, which differ from SEQ ID NO: 1 or the mature polypeptide coding sequence thereof by virtue of the degeneracy of the genetic code. The present invention also relates to subsequences of SEQ ID NO: 1 that encode fragments of SEQ ID NO: 2 having glucoamylase activity.

The present invention also relates to mutant polynucleotides comprising or consisting of at least one mutation in the mature polypeptide coding sequence of SEQ ID NO: 1, in which the mutant nucleotide sequence encodes the mature polypeptide of SEQ ID NO: 2.

The at least one mutation can be one or more (e.g., one or several) mutations. Preferably, the at least one mutation is at most 10, preferably at most 9, more preferably at most 8, more preferably at most 7, more preferably at most 6, more preferably at most 5, more preferably at most 4, even more preferably at most 3, most preferably at most 2, and even most preferably at most 1 mutation. Preferably the mutation is the nucleotide substitution, deletion and/or insertion.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application,* Academic Press, New York. Other nucleic acid amplification procedures such as ligase chain reaction (LCR), ligation activated transcription (LAT) and nucleotide sequence-based amplification (NASBA) may be used. The polynucleotides may be cloned from a strain of *Penicillium,* or another or related organism and thus, for example, may be an allelic or species variant of the polypeptide encoding region of the nucleotide sequence.

The present invention also relates to isolated polynucleotides comprising or consisting of nucleotide sequences having a degree of sequence identity to the mature polypeptide coding sequence of SEQ ID NO: 1 of preferably at least 61.5%, more preferably at least 63%, more preferably at least 65%, more preferably at least 68%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which encode a polypeptide having glucoamylase activity.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the mature polypeptide coding sequence of SEQ ID NO: 1, e.g., a subsequence thereof, and/or by introduction of nucleotide substitutions that do not give rise to another amino acid sequence of the polypeptide encoded by the nucleotide sequence, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, supra). In the latter technique, mutations are introduced at every positively charged residue in the molecule, and the resultant mutant molecules are tested for glucoamylase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labeling (see, e.g., de Vos et al., 1992, supra; Smith et al., 1992, supra; Wlodaver et al., 1992, supra).

In a preferred aspect, the present invention also relates to isolated polynucleotides encoding polypeptides of the present invention, which hybridize under preferably very low stringency conditions, more preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, (ii) the genomic DNA sequence comprising the mature polypeptide coding sequence of SEQ ID NO: 1, or (iii) a full-length complementary strand of (i) or (ii); or allelic variants and subsequences thereof (Sambrook et al., 1989, supra), as defined herein.

In a preferred aspect, the present invention also relates to isolated polynucleotides obtained by (a) hybridizing a population of DNA under preferably very low stringency conditions, more preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, (ii) the genomic DNA sequence comprising the mature polypeptide coding sequence of SEQ ID NO: 1, or (iii) a full-length complementary strand of (i) or (ii); and (b) isolating the hybridizing polynucleotide, which encodes a polypeptide having glucoamylase activity.

Nucleic Acid Constructs

The present invention also relates to nucleic acid constructs comprising an isolated polynucleotide of the present invention operably linked to one or more (e.g., several) control sequences that direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence that is recognized by a host cell for expression of a polynucleotide encoding a polypeptide of the present invention. The promoter sequence contains transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as a NA2-tpi promoter (a modified promoter including a gene encoding a neutral alpha-amylase in *Aspergilli* in which the untranslated leader has been replaced by an untranslated leader from a gene encoding triose phosphate isomerase in *Aspergilli;* non-limiting examples include modified promoters including the gene encoding neutral alpha-amylase in *Aspergillus niger* in which the untranslated leader has been replaced by an untranslated leader from the gene encoding triose phosphate isomerase in *Aspergillus nidulans* or *Aspergillus oryzae*); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator that is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, when transcribed is a nontranslated region of an mRNA that is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and, when transcribed, is recognized by the host cell as a signal to add polyadenosine residues to transcribed mRNA. Any polyadenylation sequence that is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding sequence that encodes a signal peptide linked to the amino terminus of a polypeptide and directs the encoded polypeptide into the cell's secretory pathway. The 5' end of the coding sequence of the nucleotide sequence may inherently contain a signal peptide coding sequence naturally linked in translation reading frame with the segment of the coding sequence that encodes the secreted polypeptide. Alternatively, the 5' end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice, i.e., secreted into a culture medium, may be used in the present invention.

Effective signal peptide coding sequences for filamentous fungal host cells are the signal peptide coding sequences obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

In a preferred aspect, the signal peptide comprises or consists of amino acids 1 to 21 of SEQ ID NO: 2. In another preferred aspect, the signal peptide coding sequence comprises or consists of nucleotides 1 to 63 of SEQ ID NO: 1.

The control sequence may also be a propeptide coding sequence that encodes a propeptide positioned at the amino terminus of a polypeptide. The resultant polypeptide is known as a proenzyme or propolypeptide (or a zymogen in some cases). A propeptide is generally inactive and can be converted to a mature active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide sequences are present at the amino terminus of a polypeptide, the propeptide sequence is positioned next to the amino terminus of a polypeptide and the signal peptide sequence is positioned next to the amino terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, preferably futher comprising a promoter, and transcriptional and translational stop signals. The various nucleic acids and control sequences described herein may be joined together to produce a recombinant expression vector that may include one or more (e.g., several) convenient restriction sites to allow for insertion or substitution of the nucleotide sequence encoding the polypeptide at such sites. Alternatively, a polynucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vectors of the present invention preferably contain one or more (e.g., several) selectable markers that permit easy selection of transformed, transfected, transduced, or the like cells. A selectable marker is a gene the product of which provides for biocide or viral resistance, resistance to heavy metals, prototrophy to auxotrophs, and the like.

Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli,* and pUB110, pE194, pTA1060, and pAMß1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising the nucleic acid construct of the present invention. A construct or vector comprising a polynucleotide of the present invention is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram positive bacterium or a Gram negative bacterium. Gram positive bacteria include, but not limited to, *Bacillus, Streptococcus, Streptomyces, Staphylococcus, Enterococcus, Lactobacillus, Lactococcus, Clostridium, Geobacillus,* and *Oceanobacillus*. Gram negative bacteria include, but not limited to, *E. coli, Pseudomonas, Salmonella, Campylobacter, Helicobacter, Flavobacterium, Fusobacterium, Ilyobacter, Neisseria,* and *Ureaplasma*.

The introduction of DNA into a *Bacillus* cell may, for instance, be effected by protoplast transformation (see, e.g., Chang and Cohen, 1979, *Molecular General Genetics* 168: 111-115), by using competent cells (see, e.g., Young and Spizizen, 1961, *Journal of Bacteriology* 81: 823-829, or Dubnau and Davidoff-Abelson, 1971, *Journal of Molecular Biology* 56: 209-221), by electroporation (see, e.g., Shigekawa and Dower, 1988, *Biotechniques* 6: 742-751), or by conjugation (see, e.g., Koehler and Thorne, 1987, *Journal of Bacteriology* 169: 5271-5278). The introduction of DNA into an *E coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol. (Praha)* 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios.* 68: 189-207, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

In a preferred aspect, the host cell is a fungal cell. "Fungi" as used herein includes the phyla *Ascomycota, Basidiomycota, Chytridiomycota,* and *Zygomycota* (as defined by Hawksworth et al., In, *Ainsworth and Bisby's Dictionary of The Fungi,* 8th edition, 1995, CAB International, University Press, Cambridge, UK) as well as the *Oomycota* (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (*Endomycetales*), basidiosporogenous yeast, and yeast belonging to the Fungi Imperfecti (*Blastomycetes*). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium* Series No. 9, 1980).

In an even more preferred aspect, the yeast host cell is a *Candida, Hansenula, Kluyveromyces, Pichia, Saccharomyces, Schizosaccharomyces,* or *Yarrowia* cell.

In a most preferred aspect, the yeast host cell is a *Saccharomyces carlsbergensis* cell. In another most preferred aspect, the yeast host cell is a *Saccharomyces cerevisiae* cell. In another most preferred aspect, the yeast host cell is a *Saccharomyces diastaticus* cell. In another most preferred aspect, the yeast host cell is a *Saccharomyces douglasii* cell. In another most preferred aspect, the yeast host cell is a *Saccharomyces kluyveri* cell. In another most preferred aspect, the yeast host cell is a *Saccharomyces norbensis* cell. In another most preferred aspect, the yeast host cell is a *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision *Eumycota* and *Oomycota* (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium suiphureum, Fusarium torulosum, Fusarium trichothecioides,* or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phiebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

In another most preferred aspect, the filamentous fungal host cell is an *Aspergillus niger* cell. In another most preferred aspect, the filamentous fungal host cell is an *Aspergillus oryzae* cell. In another most preferred aspect, the filamentous fungal host cell is a *Chrysosporium lucknowense* cell. In another most preferred aspect, the filamentous fungal host cell is a *Fusarium venenatum* cell. In another a most preferred spect, the filamentous fungal host cell is a *Myceliophthora thermophila* cell. In another most preferred aspect, the filamentous fungal host cell is a *Trichoderma reesei* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In a preferred aspect, the cell is of the genus *Penicillium*. In a more preferred aspect, the cell is *Penicillium* oxalicum. In a most preferred aspect, the cell is *Penicillium oxalicum* comprising the glucoamylase gene in the plasmid AMG 1 which is contained in *E. coli* DSM 23123.

The present invention also relates to methods of producing a polypeptide of the present invention, comprising: (a) cultivating a host cell comprising a nucleic acid construct comprising a polynucleotide encoding a polypeptide of the present invention, under conditions conducive for production of the polypeptide; and (b) recovering the polypeptide.

The present invention also relates to methods of producing a polypeptide of the present invention, comprising: (a) cultivating a recombinant host cell under conditions conducive for production of the polypeptide, wherein the host cell comprises a mutant nucleotide sequence having at least one mutation in the mature polypeptide coding sequence of SEQ ID NO: 1, wherein the mutant nucleotide sequence encodes a polypeptide that comprises or consists of the mature polypeptide of SEQ ID NO: 2; and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted into the medium, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

The present invention also relates to methods of producing a polypeptide of the present invention, comprising: (a) cultivating a transgenic plant or a plant cell comprising a polynucleotide encoding the polypeptide under conditions conductive for production of the polypeptide; and (b) recovering the polypeptide.

Plants

The present invention also relates to plants, e.g., a transgenic plant, plant part, or plant cell, transformed with a polynucleotide encoding a polypeptide having glucoamylase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium,* temperate grass, such as *Agrostis,* and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide of the present invention may be constructed in accordance with methods known in the art. In short, the plant or plant cell is constructed by incorporating one or more (e.g., several) expression constructs encoding a polypeptide of the present invention into the plant host genome or chloroplast genome and propagating the resulting modified plant or plant cell into a transgenic plant or plant cell.

The expression construct is conveniently a nucleic acid construct that comprises a polynucleotide encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from Vicia faba (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the chlorella virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron that is placed between the promoter and the nucleotide sequence encoding a polypeptide of the present invention. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428. Additional transformation methods for use in accordance with the present disclosure include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well-known in the art. Often the transformation procedure is designed for the selective elimination of selection genes either during regeneration or in the following generations by using, for example, co-transformation with two separate T-DNA constructs or site specific excision of the selection gene by a specific recombinase.

The present invention also relates to methods of producing a polypeptide of the present invention comprising: (a) cultivating a transgenic plant or a plant cell comprising a polynucleotide encoding the polypeptide having glucoamylase activity of the present invention under conditions conducive for production of the polypeptide; and (b) recovering the polypeptide.

In addition to direct transformation of a particular plant genotype with a construct prepared according to the present invention, transgenic plants may be made by crossing a plant having a construct of the present invention to a second plant lacking the construct. For example, a construct encoding a polypeptide having glucoamylase activity or a portion thereof can be introduced into a particular plant variety by crossing, without the need for ever directly transforming a plant of that given variety. Therefore, the present invention not only encompasses a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention, or a portion of a DNA construct prepared in accordance with the present invention. Crossing results in a transgene of the present invention being introduced into a plant line by cross pollinating a starting line with a donor plant line that includes a transgene of the present invention. Non-limiting examples of such steps are further articulated in U.S. Pat. No. 7,151,204.

It is envisioned that plants including a polypeptide having glucoamylase activity of the present invention include plants generated through a process of backcross conversion. For examples, plants of the present invention include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

Compositions

The present invention also relates to compositions comprising a polypeptide of the present invention and preferably a carrier and/or an excipient. Preferably, the compositions are enriched in such a polypeptide. The term "enriched"

indicates that the glucoamylase activity of the composition has been increased, e.g., with an enrichment factor of at least 1.1. Preferably, the compositions are formulated to provide desirable characteristics such as low color, low odor and acceptable storage stability.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus,* preferably *Aspergillus aculeatus, Aspergillus awamori, Aspergillus fumigatus, Aspergillus foetidus, Aspergillus japonicus, Aspergillus nidulans, Aspergillus niger,* or *Aspergillus oryzae; Fusarium,* preferably *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium suiphureum, Fusarium toruloseum, Fusarium trichothecioides,* or *Fusarium venenatum; Humicola,* preferably *Humicola insolens* or *Humicola lanuginosa;* or *Trichoderma,* preferably *Trichoderma harzianum, Trichoderma koningii, Trichoderma longibrachiatum, Trichoderma reesei,* or *Trichoderma viride.*

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide or polypeptide compositions of the invention. The dosage of the polypeptide composition of the invention and other conditions under which the composition is used may be determined on the basis of methods known in the art.

Combination of Glucoamylase and Alpha-Amylase

According to this aspect of the invention a glucoamylase of the invention may be combined with an alpha-amylase. Preferably, the ratio of acid alpha-amylase to glucoamylase is between 0.05 and 5.0 AFAU/AGU. More preferably the ratio between acid alpha-amylase activity and glucoamylase activity is at least 0.10, at least 0.15, at least 0.20, at least 0.25, at least 0.30, at least 0.35, at least 0.40, at least 0.45, at least 0.50, at least 0.55, at least 0.60, at least 0.65, at least 0.70, at least 0.75, at least 0.80, at least 0.85, at least 0.90, at least 0.95, at least 1.00, at least 1.05, at least 1.10, at least 1.20, at least 1.30, at least 1.40, at least 1.50, at least 1.60, at least 1.70, at least 1.80, at least 1.85, or even at least 1.90 AFAU/AGU. However, the ratio between acid alpha-amylase activity and glucoamylase activity should preferably be less than 4.50, less than 4.00, less than 3.50, less than 3.00, less than 2.50, or even less than 2.25 AFAU/AGU.

Above composition is suitable for use in liquefaction, saccharification, and/or fermentation process, preferably in starch conversion, especially for producing syrup and fermentation products, such as ethanol.

Examples are given below of preferred uses of the polypeptide compositions of the present invention. The dosage of the polypeptide composition of the invention and other conditions under which the composition is used may be determined on the basis of methods known in the art.

Uses

The present invention is also directed to use of a polypeptide of the present invention in a liquefaction, a saccharification and/or a fermentation process. The polypeptide may be used in a single process, for example, in a liquefaction process, a saccharification process, or a fermentation process. The polypeptide may also be used in a combination of processes for example in a liquefaction and saccharification process, in a liquefaction and fermentation process, or in a saccharification and fermentation process, preferably in relation to starch conversion.

In a preferred aspect of the present invention, the liquefaction, saccharification and/or fermentation process includes sequentially or simultaneously performed liquefaction and saccharification processes.

In conventional enzymatic liquefaction process, thermostable alpha-amylase is added and the long chained starch is degraded into branched and linear shorter units (maltodextrins), but glucoamylase is not added. The glucoamylase of the present invention is highly thermostable, so it is advantageous to add the glucoamylase in the liquefaction process. The glucoamylase of the present invention has a synergistic effect when combined with an alpha-amylase in the liquefaction process. During conventional saccharification, the dextrins generated during the liquefaction process are further hydrolyzed to produce low molecular sugars DP1-3 that can be metabolized by fermenting organism. The hydrolysis is typically accomplished using glucoamylases; alternatively in addition to glucoamylases, alpha-glucosidases and/or acid alpha-amylases can be used.

When applying the glucoamylase of the present invention, potentially in combination with an alpha-amylase in a liquefaction and/or saccharification process, especially in a simultaneous liquefaction and saccharification process, the process can be conducted at a higher temperature. By conducting the liquefaction and/or saccharification processs at higher temperatures the process can be carried out in a shorter period of time or alternatively the process can be carried out using lower enzyme dosage. Furthermore, the risk of microbial contamination is reduced when carrying the liquefaction and/or saccharification process at higher temperature.

Conversion of Starch-Containing Material

The present invention provides a use of the glucoamylase of the invention for producing glucoses and the like from starch. Generally, the method includes the steps of partially hydrolyzing precursor starch using glucoamylase of the present invention either alone or in the presence of an alpha-amylase.

The glucoamylase of the invention may also be used in combination with an enzyme that hydrolyzes only alpha-(1,6)-glucosidic bonds in molecules comprising at least four glucosyl residues. Preferably, the glucoamylase of the invention is used in combination with pullulanase or isoamylase. The use of isoamylase and pullulanase for debranching of starch, the molecular properties of the enzymes, and the potential use of the enzymes together with glucoamylase is described in G. M. A. van Beynum et al., Starch Conversion Technology, Marcel Dekker, New York, 1985, 101-142.

In a further aspect the invention relates to the use of a glucoamylase of the invention in starch conversion. Furthermore, the glucoamylase of the invention may be used in a continuous starch conversion process including a continuous saccharification process.

Production of Syrup, Beverage and/or Fermentation Product

Uses of the glucoamylase of the invention include conversion of starch to e.g., syrup beverage, and/or a fermentation product, including ethanol.

The present invention also provides a process of using a glucoamylase of the invention for producing syrup, such as glucose and the like, from starch-containing material. Suitable starting materials are exemplified in the "Starch-containing materials"-section. Generally, the process comprises the steps of partially or totally hydrolyzing starch-containing material (liquefaction and/or saccharification) in the presence of the glucoamylase of the present invention alone or in combination with alpha-amylase to release glucose from the non-reducing ends of the starch or related oligo- and poly-saccharide molecules.

The glucoamylase of the invention may also be used in immobilized form. This is suitable and often used for producing speciality syrups, such as maltose syrups as well as in the raffinate stream of oligosaccharides in connection with the production of fructose syrups, e.g., high fructose syrup (HFS).

The glucoamylase of the present invention can also be used for producing various beverages, such as, but not limited to, the beverage of tomato, potato, Chinese potato, sweet potato, and/or pumpkin.

Fermentation Products

The term "fermentation product" means a product produced by a process including a fermentation process using a fermenting organism. Fermentation products contemplated according to the invention include alcohols (e.g., arabinitol, butanol, ethanol, glycerol, methanol, ethylene glycol, 1,3-propanediol [propylene glycol], butanediol, glycerin, sorbitol, and xylitol); organic acids (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); ketones (e.g., acetone); amino acids (e.g., aspartic acid, glutamic acid, glycine, lysine, serine, and threonine); an alkane (e.g., pentane, hexane, heptane, octane, nonane, decane, undecane, and dodecane); a cycloalkane (e.g., cyclopentane, cyclohexane, cycloheptane, and cyclooctane); an alkene (e.g. pentene, hexene, heptene, and octene); gases (e.g., methane, hydrogen ($H_2$), carbon dioxide ($CO_2$), and carbon monoxide (CO)); antibiotics (e.g., penicillin and tetracycline); enzymes; vitamins (e.g., riboflavin, $B_{12}$, beta-carotene); and hormones. In a preferred aspect the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. Preferred fermentation processes used include alcohol fermentation processes, which are well known in the art. Preferred fermentation processes are anaerobic fermentation processes, which are well known in the art.

Brewing

The glucoamylases of the present invention are highly thermostable and therefore they can be used in an industry which needs starch hydrolysis at high temperature. For example, glucoamylases of the invention can be used in a brewing industry. The glucoamylases of the invention is added in effective amounts which can be easily determined by the skilled person in the art.

Production of a Liquefaction, Saccharification and/or Fermentation Product

In this aspect the present invention relates to a process for producing a liquefaction, saccharification and/or fermentation product from starch-containing material, comprising the step of: treating starch-containing material with a polypeptide of the present invention.

Suitable starch-containing starting materials are listed in the "Starch-containing materials"-section below. Contemplated enzymes are listed in the "Enzymes"—section below. Preferably the process of present invention comprises treating starch-containing material with a polypeptide of the present invention alone or together with an alpha-amylase. Preferably, the step of treating starch-containing material with a polypeptide of the present invention (alone or in the presence of alpha-amylase) is carried out at temperatures between 40° C. and 100° C., preferably between 65° C. and 90° C., more preferably between 80° C. and 85° C., and/or at a pH between 2.0 and 7.0, preferably between pH 4.0 and pH 6.0, more preferably between pH 4.5 and pH 5.5.

The liquefaction and/or saccharification product of the present invention are dextrin, or low molecular sugars, for example DP1-3. In the liquefaction process the conversion of starch into glucose, dextrin and/or low molecular weight sugars is enhanced by the addition of a glucoamylase of the present invention. The fermentation product, such as ethanol, may optionally be recovered after fermentation, e.g., by distillation. The fermentation is preferably carried out in the presence of yeast, preferably a strain of *Saccharomyces*. Suitable fermenting organisms are listed in the "Fermenting Organisms"—section below.

The most widely used process in fermentation product, especially ethanol, production is the simultaneous saccharification and fermentation (SSF) process, in which fermenting organism(s), such as yeast(s), and saccharification enzyme(s) may be added together. SSF may typically be carried out at a temperature between 25° C. and 40° C., such as between 29° C. and 35° C., such as between 30° C. and 34° C., such as around 32° C. According to the invention the temperature may be adjusted up or down during fermentation. The glucoamylase of the present invention when used in liquefaction process can nicely enhance ethanol production. The glycoamylase of the present invention could accelerate fermentation rate when added together with alpha-amylase, and final ethanol titers could also be increased.

The conventional saccharification may be carried out using conditions well know in the art. For instance, a full saccharification process may last up to from about 24 to about 72 hours, however, it is common only to do a pre-saccharification of typically 40-90 minutes at a temperature between 30-65° C., typically about 60° C., followed by complete saccharification during fermentation in a simultaneous saccharification and fermentation (SSF). Saccharification is typically carried out at temperatures from 30-65° C., typically around 60° C. The glucoamylase of the present invention is highly thermostable, so the pre-saccharification and/or saccharification of the present invention can be carried at a higher temperature than the conventional pre-saccharification and/or saccharification. In one embodiment a process of the invention includes pre-saccharifying starch-containing material before simultaneous saccharification and fermentation (SSF) process. The pre-saccharification can be carried out at a high temperature (for example, 50-85° C., preferably 60-75° C.) before moving into SSF. The starch-containing material may be prepared by reducing the particle size, preferably by wet milling, to 0.05 to 3.0 mm, preferably 0.1-0.5 mm. After being subjected to a process of the invention at least 85%, at least 86%, at least 87%, at least 88%, at least 89%, at least 90%, at least 91%, at least 92%, at least 93%, at least 94%, at least 95%, at least 96%, at least 97%, at least 98%, preferably at least 99%, and even more preferably 100% of the dry solids of the starch-containing material is converted into a soluble starch hydrolysate.

In one embodiment a process of the invention includes saccharifying starch-containing material, e.g. DE11 (dextrose equivalent 11) Maltodextrin, in the presence of a glucoamylase of the invention to produce sugars that can be fermented into the desired fermentation product by a suitable fermenting organism.

The fermentation process may be carried out for a period of 1 to 250 hours, preferably is from 25 to 190 hours, more preferably from 30 to 180 hours, more preferably from 40 to 170 hours, even more preferably from 50 to 160 hours, yet more preferably from 50 to 130 hours.

A slurry of starch-containing material, such as granular starch, having 10-55 wt % dry solids (DS), preferably 25-40 wt % dry solids, more preferably 30-35wt % dry solids of starch-containing material may be prepared. The slurry may include water and/or process waters, such as stillage (backset), scrubber water, evaporator condensate or distillate, side stripper water from distillation, or other fermentation product plant process water.

After being subjected to a process of the invention at least 85%, at least 86%, at least 87%, at least 88%, at least 89%, at least 90%, at least 91%, at least 92%, at least 93%, at least 94%, at least 95%, at least 96%, at least 97%, at least 98%, preferably at least 99%, and even more preferably 100% of the dry solids of the starch-containing material is converted into a soluble starch hydrolysate.

Starch-Containing Materials

Any suitable starch-containing starting material, including granular starch, may be used according to the present invention. The starting material is generally selected based on the desired fermentation product. Examples of starch-containing starting materials, suitable for use in a process of present invention, include tubers, roots, stems, whole grains, corns, cobs, wheat, barley, rye, milo, sago, cassava, tapioca, sorghum, rice peas, beans, or sweet potatoes, or mixtures thereof, or cereals, sugar-containing raw materials, such as molasses, fruit materials, sugar cane or sugar beet, potatoes, and cellulose-containing materials, such as wood or plant residues, or mixtures thereof. Contemplated are both waxy and non-waxy types of corn and barley.

Fermenting Organisms

"Fermenting organism" refers to any organism, including bacterial and fungal organisms, suitable for use in a fermentation process and capable of producing desired a fermentation product. Especially suitable fermenting organisms are able to ferment, i.e., convert, sugars, such as glucose or maltose, directly or indirectly into the desired fermentation product. Examples of fermenting organisms include fungal organisms, such as yeast. Preferred yeast includes strains of *Saccharomyces* spp., in particular, *Saccharomyces cerevisiae*. Commercially available yeast include, e.g., Red Star™/Lesaffre Ethanol Red (available from Red Star/ Lesaffre, USA) FALI (available from Fleischmann's Yeast, a division of Burns Philp Food Inc., USA), SUPERSTART (available from Alltech), GERT STRAND (available from Gert Strand AB, Sweden) and FERMIOL (available from DSM Specialties).

Enzymes

Glucoamylase

The glucoamylase is preferably a glucoamylase of the invention. However, as mentioned above a glucoamylase of the invention may also be combined with other glucoamylases.

The glucoamylase may added in an amount of 0.001 to 10 AGU/g DS, preferably from 0.01 to 5 AGU/g DS, such as around 0.05, 0.1, 0.3, 0.5, 1 or 2 AGU/g DS, especially 0.05 to 0.5 AGU/g DS; or 0.02-20 AGU/g DS, preferably 0.1-10 AGU/g DS.

Alpha-Amylase

The alpha-amylase may according to the invention be of any origin. Preferred are alpha-amylases of fungal or bacterial origin.

In a preferred aspect the alpha-amylase is an acid alpha-amylase, e.g., fungal acid alpha-amylase or bacterial acid alpha-amylase. The term "acid alpha-amylase" means an alpha-amylase (E.C. 3.2.1.1) which added in an effective amount has activity optimum at a pH in the range of 3 to 7, preferably from 3.5 to 6, or more preferably from 4-5.

Bacterial Alpha-Amylases

According to the invention a bacterial alpha-amylase may preferably be derived from the genus *Bacillus*.

In a preferred aspect the *Bacillus* alpha-amylase is derived from a strain of *B. licheniformis, B. amyloliquefaciens, B. subtilis* or *B. stearothermophilus*, but may also be derived from other *Bacillus* sp. Specific examples of contemplated alpha-amylases include the *Bacillus licheniformis* alpha-amylase (BLA) shown in SEQ ID NO: 4 in WO 99/19467, the *Bacillus amyloliquefaciens* alpha-amylase (BAN) shown in SEQ ID NO: 5 in WO 99/19467, and the *Bacillus stearothermophilus* alpha-amylase (BSG) shown in SEQ ID NO: 3 in WO 99/19467. In an embodiment of the invention the alpha-amylase is an enzyme having a degree of identity of at least 60%, preferably at least 70%, more preferred at least 80%, even more preferred at least 90%, such as at least 95%, at least 96%, at least 97%, at least 98% or at least 99% identity to any of the sequences shown as SEQ ID NOS: 1, 2, 3, 4, or 5, respectively, in WO 99/19467.

The *Bacillus* alpha-amylase may also be a variant and/or hybrid, especially one described in any of WO 96/23873, WO 96/23874, WO 97/41213, WO 99/19467, WO 00/60059, and WO 02/10355 (all documents hereby incorporated by reference). Specifically contemplated alpha-amylase variants are disclosed in U.S. Pat. Nos. 6,093,562, 6,297,038 or 6,187,576 (hereby incorporated by reference) and include *Bacillus stearothermophilus* alpha-amylase (BSG alpha-amylase) variants having a deletion of one or two amino acid in position 179 to 182, preferably a double deletion disclosed in WO 1996/023873—see e.g., page 20, lines 1-10 (hereby incorporated by reference), preferably corresponding to delta(181-182) compared to the wild-type BSG alpha-amylase amino acid sequence set forth in SEQ ID NO: 3 disclosed in WO 99/19467 or deletion of amino acids 179 and 180 using SEQ ID NO: 3 in WO 99/19467 for numbering (which reference is hereby incorporated by reference). Even more preferred are *Bacillus* alpha-amylases, especially *Bacillus stearothermophilus* alpha-amylase, which have a double deletion corresponding to delta(181-182) and further comprise a N193F substitution (also denoted I181*+G182*+N193F) compared to the wild-type BSG alpha-amylase amino acid sequence set forth in SEQ ID NO: 3 disclosed in WO 99/19467.

The alpha-amylase may also be a maltogenic alpha-amylase. A "maltogenic alpha-amylase" (glucan 1,4-alpha-maltohydrolase, E.C. 3.2.1.133) is able to hydrolyze amylose and amylopectin to maltose in the alpha-configuration. A maltogenic alpha-amylase from *Bacillus stearothermophilus* strain NCIB 11837 is commercially available from Novozymes A/S, Denmark. The maltogenic alpha-amylase is described in U.S. Pat. Nos. 4,598,048, 4,604,355 and 6,162,628, which are hereby incorporated by reference.

Bacterial Hybrid Alpha-Amylases

A hybrid alpha-amylase specifically contemplated comprises 445 C-terminal amino acid residues of the *Bacillus licheniformis* alpha-amylase (shown as SEQ ID NO: 4 in WO 99/19467) and the 37 N-terminal amino acid residues of the alpha-amylase derived from *Bacillus amyloliquefaciens* (shown as SEQ ID NO: 3 in WO 99/194676), with one or more, especially all, of the following substitution:

G48A+T49I+G107A+H156Y+A181T+N190F+I201F+A209V+Q264S (using the *Bacillus licheniformis* numbering). Also preferred are variants having one or more of the following mutations (or corresponding mutations in other *Bacillus* alpha-amylase backbones): H154Y, A181T, N190F, A209V and Q264S and/or deletion of two residues between positions 176 and 179, preferably deletion of E178 and G179 (using the SEQ ID NO: 5 numbering of WO 99/19467).

Fungal Alpha-Amylases

Fungal acid alpha-amylases include acid alpha-amylases derived from a strain of the genus *Aspergillus*, such as *Aspergillus oryzae*, *Aspergillus niger*, or *Aspergillus kawachii* alpha-amylases.

A preferred acid fungal alpha-amylase is a Fungamyl-like alpha-amylase which is preferably derived from a strain of *Aspergillus oryzae*. In the present disclosure, the term "Fungamyl-like alpha-amylase" indicates an alpha-amylase which exhibits a high identity, i.e. more than 70%, more than 75%, more than 80%, more than 85% more than 90%, more than 95%, more than 96%, more than 97%, more than 98%, more than 99% or even 100% identity to the mature part of the amino acid sequence shown in SEQ ID NO: 10 in WO 96/23874.

Another preferred acid alpha-amylase is derived from a strain *Aspergillus niger*. In a preferred aspect the acid fungal alpha-amylase is the one from *A. niger* disclosed as "AMYA_ASPNG" in the Swiss-prot/TeEMBL database under the primary accession no. P56271 and described in more detail in WO 89/01969 (Example 3). The acid *Aspergillus niger* acid alpha-amylase is also shown as SEQ ID NO: 1 in WO 2004/080923 (Novozymes) which is hereby incorporated by reference. Also variants of said acid fungal amylase having at least 70% identity, such as at least 80% or even at least 90% identity, such as at least 95%, at least 96%, at least 97%, at least 98%, or at least 99% identity to SEQ ID NO: 1 in WO 2004/080923 are contemplated.

In a preferred aspect the alpha-amylase is derived from *Aspergillus kawachii* and disclosed by Kaneko et al. J. Ferment. Bioeng. 81:292-298(1996) "Molecular-cloning and determination of the nucleotide-sequence of a gene encoding an acid-stable alpha-amylase from *Aspergillus kawachii*"; and further as EMBL:#AB008370.

The fungal acid alpha-amylase may also be a wild-type enzyme comprising a carbohydrate-binding module (CBM) and an alpha-amylase catalytic domain (i.e., a none-hybrid), or a variant thereof. In an embodiment the wild-type acid alpha-amylase is derived from a strain of *Aspergillus kawachii*.

An acid alpha-amylases may according to the invention be added in an amount of 0.01 to 10 AFAU/g DS, preferably 0.01 to 5 AFAU/g DS, especially 0.02 to 2 AFAU/g DS.

Fungal Hybrid Alpha-Amylases

In a preferred aspect the fungal acid alpha-amylase is a hybrid alpha-amylase. Preferred examples of fungal hybrid alpha-amylases include the ones disclosed in WO 2005/003311 or U.S. Patent Publication no. 2005/0054071 (Novozymes) or US patent application No. 2006/0148054 (Novozymes) which is hereby incorporated by reference. A hybrid alpha-amylase may comprise an alpha-amylase catalytic domain (CD) and a carbohydrate-binding domain/module (CBM) and optional a linker.

Specific examples of contemplated hybrid alpha-amylases include, but not limited to those disclosed in U.S. patent application No. 2006/0148054 including Fungamyl variant with catalytic domain JA118 and *Athelia rolfsii* SBD (SEQ ID NO: 100 in U.S. application No. 2006/0148054), *Rhizomucor pusillus* alpha-amylase with *Athelia rolfsii* AMG linker and SBD (SEQ ID NO: 101 in U.S. application No. 2006/0148054)and *Meripilus giganteus* alpha-amylase with *Athelia rolfsii* glucoamylase linker and SBD (SEQ ID NO: 102 in U.S. application No. 2006/0148054); and *Rhizomucor pusillus* alpha-amylase with *Aspergillus niger* glucoamylase linker and CBM (SEQ ID NO 2 in international publication No. WO2007/144424).

Other specific examples of contemplated hybrid alpha-amylases include, but not limited to those disclosed in U.S. Patent Publication no. 2005/0054071, including those disclosed in Table 3 on page 15, such as *Aspergillus niger* alpha-amylase with *Aspergillus kawachii* linker and starch binding domain.

Commercial Alpha-Amylase Products

Preferred commercial compositions comprising alpha-amylase include MYCOLASE from DSM (Gist Brocades), BAN™, TERMAMYL™ SC, FUNGAMYL™, LIQUOZYME™ X and SAN™ SUPER, SAN™ EXTRA L (Novozymes A/S) and CLARASE™ L-40,000, DEX-LO™, SPEZYME™ FRED, SPEZYME™ AA, SPEZYME™ Ethyl, and SPEZYME™ DELTA AA (Genencor Int.).

Materials and Methods

Glucoamylase Activity

Glucoamylase activity may be measured in AGU Units.

Glucoamylase Activity (AGU)

The Glucoamylase Unit (AGU) is defined as the amount of enzyme, which hydrolyzes 1 micromole maltose per minute under the standard conditions (37° C., pH 4.3, substrate: maltose 100 mM, buffer: acetate 0.1 M, reaction time 6 minutes as set out in the glucoamylase incubation below), thereby generating glucose.

| ducoamylase incubation: | |
| --- | --- |
| Substrate: | maltose 100 mM |
| Buffer: | acetate 0.1M |
| pH: | 4.30 ± 0.05 |
| Incubation temperature: | 37° C. ± 1 |
| Reaction time: | 6 minutes |
| Enzyme working range: | 0.5-4.0 AGU/mL |

The analysis principle is described by 3 reaction steps:

Step 1 is an enzyme reaction:

Glucoamylase (AMG), EC 3.2.1.3 (exo-alpha-1,4-glucan-glucohydrolase), hydrolyzes maltose to form alpha-D-glucose. After incubation, the reaction is stopped with NaOH.

Step 2 and 3 result in an endpoint reaction:

Glucose is phosphorylated by ATP, in a reaction catalyzed by hexokinase. The glucose-6-phosphate formed is oxidized to 6-phosphogluconate by glucose-6-phosphate dehydrogenase. In this same reaction, an equimolar amount of NAD+ is reduced to NADH with a resulting increase in absorbance at 340 nm. An autoanalyzer system such as Konelab 30 Analyzer (Thermo Fisher Scientific) may be used.

| Colour reaction | |
|---|---|
| Tris | approx. 35 mM |
| ATP | 0.7 mM |
| NAD+ | 0.7 mM |
| $Mg^{2+}$ | 1.8 mM |
| Hexokinase | >850 U/L |
| Glucose-6-P-DH | >850 U/L |
| pH | approx. 7.8 |
| Temperature | 37.0° C. ± 1.0° C. |
| Reaction time | 420 sec |
| Wavelength | 340 nm |

Acid Alpha-Amylase Activity

When used according to the present invention the activity of any acid alpha-amylase may be measured in AFAU (Acid Fungal Alpha-amylase Units). Alternatively activity of acid alpha-amylase may be measured in KNU-s (Kilo Novozymes Units (Termamyl SC)).

Acid Alpha-Amylase Activity (AFAU)

Acid alpha-amylase activity may be measured in AFAU (Acid Fungal Alpha-amylase Units). 1 AFAU is defined as the amount of enzyme which degrades 5.260 mg starch dry matter per hour under the below mentioned standard conditions.

Acid alpha-amylase, an endo-alpha-amylase (1,4-alpha-D-glucan-glucanohydrolase, E.C. 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

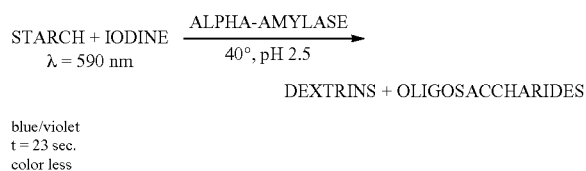

Standard Conditions/Reaction Conditions:
Substrate: Soluble starch, approx. 0.17 g/L
Buffer: Citrate, approx. 0.03 M
Iodine ($I_2$): 0.03 g/L
$CaCl_2$: 1.85 mM
pH: 2.50±0.05
Incubation temperature: 40° C.
Reaction time: 23 seconds
Wavelength: 590 nm
Enzyme concentration: 0.025 AFAU/mL
Enzyme working range: 0.01-0.04 AFAU/mL A folder EB-SM-0259.02/01 describing this analytical method in more detail is available upon request to Novozymes A/S, Denmark, which folder is hereby included by reference.

The present invention is further described by the following examples that should not be construed as limiting the scope of the invention.

Media

PDA plates were composed per liter of 39 grams of potato dextrose agar (Difco, BD213400).

NNCYP-PCS medium was composed per liter of 5.0 g of $NaNO_3$, 3.0 g of $NH_4Cl$, 2.0 g of MES (2-(N-morpholino) ethanesulfonic acid, molecuar formula: $C_6H_{13}O_4NS$ $H_2O$), 2.5 g of citric acid, 0.2 g of $CaCl_2$ $2H_2O$, 1.0 g of Bacto Peptone, 5.0 g of Yeast Extract, 0.2 g of $MgSO_4$ $7H_2O$, 4.0 g of $K_2HPO_4$, 1.0 ml of Cove Trace Elements, 2.5 g of Glucose and 25.0 g of PCS (pre-treated corn stover obtained from National Renewable Energy Laboratory (NREL)). Cove Trace Elements was composed per liter of 0.04 g of $Na_2B_4O_7.10H_2O$, 0.4 g of $CuSO4.5H_2O$, 1.2 g of $FeSO4.7H_2O$, 0.7 g of $MnSO4.H_2O$, 0.8 g of $Na_2MoO_2.2H_2O$, 10 g of $ZnSO_4.7H_2O$.

MLC medium was composed of 40 g/L Glucose, 50 g/L Soybean powder, 4 g/L Citric acid, pH 5.0.

M410 medium was composed of 50 g/L maltose-1$H_2O$, 8 g/L Yeast extract, 2 g/L $MgSO_4.7H_2O$, 4 g/L Citric acid-1$H_2O$, 50 g/L glucose, 2 g/L $K_2HPO_4$, 0.5 ml/L AMG trace metal solution, and 2 g/L urea, pH4.5. AMG trace metal solution was composed of 13.9 g/L $FeSO_4.7H_2O$, 13.5 g/L $MnSO_4.1H_2O$, 6.8 g/L $ZnCl_2$, 2.5 g/L $CuSO_4.5H_2O$, 0.24 g/L $NiCl_2.6H_2O$, and 3 g/L citric acid.

Unless otherwise stated, media are prepared according to Sambrook et al. (1989) *Molecular cloning: A laboratory manual*, Cold Spring Harbor lab., Cold Spring Harbor, N.Y. Chemicals used as buffers and substrates were commercial products of at least reagent grade.

Enzymes

Glucoamylases:

*Penicillium oxalicum* glycoamylase as disclosed in SEQ ID NO: 2 of the present invention

*Talaromyces emersonii* glucoamylase (which is disclosed in international publication WO 99/28448 as SEQ ID NO: 7)

*Aspergillus niger* glucoamylase (uniprot:P69328) (which is disclosed in Svensson, B. Larsen, K. Gunnarsson, A.; "Characterization of a glucoamylase G2 from *Aspergillus niger*."; Eur. J. Biochem. 154:497-502 (1986))

Alpha-Amylases:

Acid alpha-amylase disclosed as Variant JA001 in international publication WO 2005/003311

Alpha-amylase produced from *Bacillus licheniformis*, e.g Termamyl™ SC (commercially available alpha-amylase from Novozymes A/S, Bagsvaerd, Denmark)

EXAMPLES

Example 1

Preparation of *Penicillium oxalicum* Strain Mycelia for Total RNA Extraction

*Penicillium oxalicum* strain (which was collected in August 2008 from the soil in Yunnan province, China) was inoculated onto a PDA plate and incubated for 4 days at 25° C. in the darkness. Several mycelia-PDA plugs were inoculated into 500 ml shake flasks containing 100 ml of NNCYP-PCS medium. The flasks were incubated for 7 days at 25° C. with shaking at 160 rpm. The mycelia were collected at day 4 and day 7 respectively. Then the mycelia from each day was frozen in liquid nitrogen and stored in a −80° C. freezer until use.

Example 2

*Penicillium oxalicum* Strain RNA Preparation

The frozen mycelia were transferred into a liquid nitrogen prechilled mortar and pestle and ground to a fine powder. Total RNA was prepared from the powdered mycelia by extraction with Fenozol reagent (Active motif, Cat. No. 22100). The polyA enriched RNA was isolated by mTRAP total kit (Active Motif, Cat. No. 23012).

Example 3

Construction of a *Penicillium oxalicum* Strain cDNA Library

Double stranded cDNA of each day was synthesized with SMART cDNA library construct kit (TAKARA, Cat. No. 634901). The cDNA was cleaved with Sfi I (New England Biolabs, Cat. No. R0123S) according to the manufacturer's instructions and the cDNA was size fractionated by 0.8% agarose gel electrophoresis using in 44 mM Tris base, 44 mM boric acid, 0.5 mM EDTA (TBE) buffer. The fractions of cDNA of 500 bp and larger were excised from the gel and purified using a GFX® PCR DNA and Gel Band Purification Kit according to the manufacturer's instructions (GE, Cat. No. 28-9031-71). Then equal amounts of cDNA from day 4 and day 7 were pooled for library construction.

The prepared cDNA was then directionally cloned by ligation into Sfi I cleaved pMHas7 (described in international publication WO 2009/037253) using T4 ligase (New England Biolabs, Cat. No. M0202T) according to the manufacturer's instructions. The ligation mixture was electroporated into *E. coli* ElectroMax DH10B cells (Invitrogen, Cat. No. 18290-015) using a GENE PULSER® and Pulse Controller (Bio-Rad) at 25 uF, 25 mAmp, 1.8 kV with a 1 mm gap cuvette according to the manufacturer's procedure.

The electroporated cells were plated onto LB plates supplemented with 50 mg/L kanamycin. A cDNA plasmid pool was prepared from 50,000 total transformants of the original pMHas7 vector ligation. Plasmid DNA was prepared directly from the pool of colonies using QIAGEN plasmid kit (QIAGEN, Cat. No. 12143).

Example 4

Construction of a SigA4 Transposon Containing the β-lactamase Reporter Gene

A transposon containing plasmid designated pSigA4 was constructed from the pSigA2 transposon containing plasmid described in international publication WO 01/77315 in order to create an improved version of the signal trapping transposon of pSigA2 with decreased selection background. The pSigA2 transposon contains a signalless betalactamase construct encoded on the transposon itself. PCR was used to create a deletion of the intact beta lactamase gene found on the plasmid backbone using a proofreading Pfu Turbo polymerase ProofStart (QIAGEN GmbH Corporation, Hilden, Germany) and the following 5' phosphorylated primers (TAG Copenhagen, Denmark):

SigA2NotU-P:
(SEQ ID NO: 3)
5'-TCGCGATCCGTTTTCGCATTTATCGTGAAACGCT-3'

SigA2NotD-P:
(SEQ ID NO: 4)
5'-CCGCAAACGCTGGTGAAAGTAAAAGATGCTGAA-3'

The amplification reaction was composed of 1 µl of pSigA2 (10 ng/µl), 5 µl of 10× ProofStart Buffer (QIAGEN GmbH Corporation, Hilden, Germany), 2.5 µl of dNTP mix (20 mM), 0.5 µl of SigA2NotU-P (10 mM), 0.5 µl of SigA2NotD-P (10 mM), 10 µl of Q solution (QIAGEN GmbH Corporation, Hilden, Germany), and 31.25 µl of deionized water. A DNA ENGINE™ Thermal Cycler (MJ Research Inc., Waltham, Mass., USA) was used for amplification programmed for one cycle at 95° C. for 5 minutes; and 20 cycles each at 94° C. for 30 seconds, 62° C. for 30 seconds, and 72° C. for 4 minutes.

A 3.9 kb PCR reaction product was isolated on a 0.8% agarose gel using 40 mM Tris base-20 mM sodium acetate-1 mM disodium EDTA (TAE) buffer and 0.1 µg of ethidium bromide per ml. The DNA band was visualized with the aid of an Eagle Eye Imaging System (Stratagene, La Jolla, Calif., USA) at 360 nm. The 3.9 kb DNA band was excised from the gel and purified by using a GFX® PCR DNA and Gel Band Purification Kit (GE Healthcare, United Kingdom) according to the manufacturer's instructions.

The 3.9 kb fragment was self-ligated at 16° C. overnight with 10 units of T4 DNA ligase (New England Biolabs, Inc., Beverly, Mass., USA), 9 µl of the 3.9 kb PCR fragment, and 1 µl of 10× ligation buffer (New England Biolabs, Inc., Beverly, Mass., USA). The ligation was heat inactivated for 10 minutes at 65° C. and then digested with Dpn I at 37° C. for 2 hours. After incubation, the digestion was purified using a GFX® PCR DNA and Gel Band Purification Kit.

The purified material was then transformed into *E. coli* Top10 competent cells (Invitrogen Corp., Carlsbad, Calif., USA) according to the manufacturer's instructions. The transformation mixture was plated onto LB plates supplemented with 25 µg of chloramphenicol per ml. Plasmid minipreps were prepared from several transformants and digested with Bgl II. One plasmid with the correct construction was chosen. The plasmid was designated pSigA4. Plasmid pSigA4 contains the Bgl II flanked transposon SigA2 identical to that disclosed in WO 01/77315.

A 60 µl sample of plasmid pSigA4 DNA (0.3 µg/µl) was digested with Bgl II and separated on a 0.8% agarose gel using TBE buffer (90 mM Tris-borate; 2 mM EDTA; pH 8.0). A SigA2 transposon DNA band of 2 kb was eluted with 200 µl of EB buffer (QIAGEN GmbH Corporation, Hilden, Germany) and purified using a GFX® PCR DNA and Gel Band Purification Kit according to the manufacturer's instructions and eluted in 200 µl of EB buffer. SigA2 was used for transposon assisted signal trapping.

Example 5

Transposon Assisted Signal Trapping of *Penicillium oxalicum* Strain

A complete description of transposon assisted signal trapping can be found in WO 01/77315. The plasmid pool was treated with transposon SigA2 and HyperMu transposase (Epicenter, Cat. No. THM03210) according to the manufacturer's instructions.

For in vitro transposon tagging of the *Penicillium oxalicum* cDNA library, 2 µl of SigA2 transposon containing approximately 100 ng of DNA were mixed with 1 µl of the plasmid DNA pool of the *Penicillium oxalicum* cDNA library containing 1 µg of DNA, 1 µl of HyperMu transposase, and 2 μl of 10' buffer in a total volume of 20 μl and incubated at 30° C. for 3 hours followed by adding 2 μl of stop buffer and heat inactivation at 75° C. for 10 minutes. The DNA was precipitated by addition of 2 μl of 3 M sodium acetate pH 5 and 55 μl of 96% ethanol and centrifuged for 30 minutes at 10,000×g, 4° C. The pellet was washed in 70% ethanol, air dried at room temperature, and resuspended in 10 μl of deionized water.

A 2 μl volume of the transposon tagged plasmid pool was electroporated into 50 μl of *E. coli* ElectroMAX DH10B cells (Invitrogen) according to the manufacturer's instructions using a GENE PULSER® and Pulse Controller (Bio-Rad, Hercules, Calif., USA) at 25 uF, 25 mAmp, 1.8 kV with a 1 mm gap cuvette according to the manufacturer's procedure.

The electroporated cells were incubated in SOC medium with shaking at 225 rpm for 1 hour at 37° C. before being plated on the following selective media: LB medium supplemented with 50 μg of kanamycin per ml; LB medium supplemented with 50 μg of kanamycin per ml and 15 μg of chloramphenicol per ml; and LB medium supplemented with 50 μg of kanamycin per ml, 15 μg of chloramphenicol per ml, and 30 μg of ampicillin per ml.

From plating of the electroporation onto LB medium supplemented with kanamycin, chloramphenicol and ampicillin, approximately 700 colonies were observed after 3 days at 30° C. All colonies were replica plated on LB kanamycin, chloramphenicol with 100 mgs/l ampicillin. The colonies were sent to be sequenced by SinoGenoMax company using the transposon forward and reverse primers (primers A and B), shown below, according to the procedure disclosed in WO 01/77315 (page 28).

```
Primer A:
                                        (SEQ ID NO: 5)
5'-AGCGTTTGCGGCCGCGATCC-3'

Primer B:
                                        (SEQ ID NO: 6)
5'-TTATTCGGTCGAAAAGGATCC-3'
```

Example 6

Cloning of *Penicillium oxalicum* Strain Glucoamylase Gene

Sequence assembly and annotation. The DNA sequences were obtained from SinoGenoMax company, trimmed to remove sequence parts originating from the vector and transposon sequence. The trimmed sequences were grouped into contigs by using the program PhredPhrap (Ewing et al., 1998, Genome Research 8: 175-185; Ewing and Green, 1998, Genome Research 8: 186-194). All contigs were subsequently compared to sequences available in standard public DNA and protein sequences databases (TrEMBL, SWALL, PDB, EnsemblPep, GeneSeqP) by using the program BLASTX 2.0a19MP-WashU [14 Jul. 1998] [Build linux-x86 18:51:44 30 Jul. 1998] (Gish et al., 1993, Nat. Genet. 3: 266-72). The family GH15 glucoamylase gene was identified directly by analysis of the BlastX results.

Preparation of *Penicillium oxalicum* strain cDNA. The cDNA was synthesized by following the instruction of 3' Rapid Amplifiction of cDNA End System (Invitrogen Corp., Carlsbad, Calif., USA).

Cloning of *Penicillium oxalicum* strain glucoamylase gene. Based on the *Penicillium oxalicum* glucoamylase gene information obtained by TAST the oligonucleotide primer shown below was designed to amplify the glucoamylase gene from 5' end.

```
Sense primer:
                                        (SEQ ID NO: 7)
5'-ATGCGTCTCACTCTATTATCAGGTG-3'
```

The full length gene was amplified by PCR with Sense primer and AUAP (supplied by 3' Rapid Amplifiction of cDNA End System) by using Platinum HIFI Taq DNA polymerase (Invitrogen Corp., Carlsbad, Calif., USA). The amplification reaction was composed of 5 μl of 10× PCR buffer, 2 μl of 25 mM MgCl$_2$, 1 μl of 10 mM dNTP, 1 μl of 10 uM Sense primer, 1 μl of 10 uM AUAP, 2 μl of the first strand cDNA, 0.5 μl of HIFI Taq, and 37.5 μl of deionized water. The PCR program was: 94° C., 3 mins; 10 cycles of 94° C. for 40 secs, 60° C. 40 secs with 1° C. decrease per cycle, 68° C. for 2 min; 25 cycles of 94° C. for 40 secs, 50° C. for 40 secs, 68° C. for 2 min; final extension at 68° C. for 10 mins.

The obtained PCR fragment was cloned into pGEM-T vector (Promega Corporation, Madison, Wis., USA) using a pGEM-T Vector System (Promega Corporation, Madison, Wis., USA) to generate plasmid AMG 1. The glucoamylase gene inserted in the plasmid AMG 1 was sequencing confirmed. *E. coli* strain TOP10 containing plasmid AMG 1 (designated NN059173), was deposited with the Deutsche Sammlung von Mikroorganismen and Zellkulturen GmbH (DSMZ) on Nov. 23, 2009, and assigned accession number as DSM 23123.

Example 7

Expression of Cloned *Penicillium oxalicum* Glucoamylase

The *Penicillium oxalicum* glucoamylase gene was re-cloned from the plasmid AMG 1 into an *Aspergillus* expression vector by PCR using two cloning primer F and primer R shown below, which were designed based on the known sequence and added tags for direct cloning by IN-FUSION™ strategy.

```
Primer F:
                                        (SEQ ID NO: 8)
5' ACACAACTGGGGATCCACCATGCGTCTCACTCTATTATC Primer R:
                                        (SEQ ID NO: 9)
5' AGATCTCGAGAAGCTTAAAACTGCCACACGTCGTTGG
```

A PCR reaction was performed with plasmid AMG 1 in order to amplify the full-length gene. The PCR reaction was composed of 40 μg of the plasmid AMG 1 DNA, 1 μl of each primer (100 μM); 12.5 μl of 2× Extensor Hi-Fidelity master mix (Extensor Hi-Fidelity Master Mix, ABgene, United Kingdom), and 9.5 μl of PCR-grade water. The PCR reaction was performed using a DYAD PCR machine (Bio-Rad Laboratories, Inc., Hercules, Calif., USA) programmed for 2 minutes at 94° C. followed by a 25 cycles of 94° C. for 15 seconds, 50° C. for 30 seconds, and 72° C. for 1 minute; and then 10 minutes at 72° C.

The reaction products were isolated by 1.0% agarose gel electrophoresis using 1×TAE buffer where an approximately 1.9 kb PCR product band was excised from the gel and purified using a GFX® PCR DNA and Gel Band Purification Kit (GE Healthcare, United Kingdom) according to manufacturer's instructions. DNA corresponding to the *Penicillium oxalicum* glucoamylase gene was cloned into an *Aspergillus* expression vector linearized with BamHI and HindIII, using an INFUSION™ Dry-Down PCR Cloning Kit (BD Biosciences, Palo Alto, Calif., USA) according to the manufacturer's instructions. The linearized vector construction is as described in WO2005042735A1.

A 2 μl volume of the ligation mixture was used to transform 25 μl of Fusion Blue *E. coli* cells (included in the IN-FUSION™ Dry-Down PCR Cloning Kit). After a heat shock at 42° C. for 45 sec, and chilling on ice, 250 μl of SOC medium was added, and the cells were incubated at 37° C. at 225 rpm for 90 min before being plated out on LB agar plates containing 50 μg of ampicillin per ml, and cultivated overnight at 37° C. Selected colonies were inoculated in 3 ml of LB medium supplemented with 50 μg of ampicillin per ml and incubated at 37° C. at 225 rpm overnight. Plasmid DNA from the selected colonies was purified using Mini JETSTAR (Genomed, Germany) according to the manufacturer's instructions. *Penicillium oxalicum* glucoamylase gene sequence was verified by Sanger sequencing before heterologous expression. One of the plasmids was selected for further expression, and was named XYZ.

Protoplasts of *Aspergillus niger* MBin118 were prepared as described in WO 95/02043. One hundred μl of protoplast suspension were mixed with 2.5 μg of the XYZ plasmid and 250 microliters of 60% PEG 4000 (Applichem) (polyethylene glycol, molecular weight 4,000), 10 mM $CaCl_2$, and 10 mM Tris-HCl pH 7.5 were added and gently mixed. The mixture was incubated at 37° C. for 30 minutes and the protoplasts were mixed with 6% low melting agarose (Biowhittaker Molecular Applications) in COVE sucrose (Cove, 1996, Biochim. Biophys. Acta 133:51-56) (1M) plates supplemented with 10 mM acetamid and 15 mM CsCl and added as a top layer on COVE sucrose (1M) plates supplemented with 10 mM acetamid and 15 mM CsCl for transformants selection (4 ml topagar per plate). After incubation for 5 days at 37° C. spores of sixteen transformants were picked up and seed on 750 μl YP-2% Maltose medium in 96 deepwell MT plates. After 5 days of stationary cultivation at 30° C., 10 μl of the culture-broth from each well was analyzed on a SDS-PAGE (Sodium dodecyl sulfate-polyacrylamide gel electrophoresis) gel, Griton XT Precast gel (BioRad, CA, USA) in order to identify the best transformants based on the ability to produce large amount of glucoamylase. A selected transformant was identified on the original transformation plate and was preserved as spores in a 20% glycerol stock and stored frozen (−80° C.).

Cultivation. The selected transformant was inoculated in 100 ml of MLC media and cultivated at 30° C. for 2 days in 500 ml shake flasks on a rotary shaker. 3 ml of the culture broth was inoculated to 100 ml of M410 medium and cultivated at 30° C. for 3 days. The culture broth was centrifugated and the supernatant was filtrated using 0.2 μm membrane filters.

Alpha-cyclodextrin affinity gel. Ten grams of Epoxy-activated Sepharose 6B (GE Healthcare, Chalfont St. Giles, U.K) powder was suspended in and washed with distilled water on a sintered glass filter. The gel was suspended in coupling solution (100 ml of 12.5 mg/ml alpha-cyclodextrin, 0.5 M NaOH) and incubated at room temperature for one day with gentle shaking. The gel was washed with distilled water on a sintered glass filter, suspended in 100 ml of 1 M ethanolamine, pH 10, and incubated at 50° C. for 4 hours for blocking. The gel was then washed several times using 50 mM Tris-HCl, pH 8 and 50 mM NaOAc, pH 4.0 alternatively. The gel was finally packed in a 35-40 ml column using equilibration buffer (50 mM NaOAc, 150 mM NaCl, pH 4.5).

Purification of glucoamylase from culture broth. Culture broth from fermentation of *A. niger* MBin118 harboring the glucoamylase gene was filtrated through a 0.22 μm PES filter, and applied on a alpha-cyclodextrin affinity gel column previously equilibrated in 50 mM NaOAc, 150 mM NaCl, pH 4.5 buffer. Unbound material was washed off the column with equilibration buffer and the glucoamylase was eluted using the same buffer containing 10 mM beta-cyclodextrin over 3 column volumes.

The glucoamylase activity of the eluent was checked to see, if the glucoamylase had bound to the alpha-cyclodextrin affinity gel. The purified glucoamylase sample was then dialyzed against 20 mM NaOAc, pH 5.0. The purity was finally checked by SDS-PAGE, and only a single band was found (see FIG. 1).

Example 8

Characterization of *Penicillium oxalicum* Glucoamylase

Substrate. Substrate: 1% soluble starch (Sigma S-9765) in deionized water

Reaction buffer: 0.1M Acetate buffer at pH5.3

Glucose concentration determination kit: Wako glucose assay kit (LabAssay glucose, WAKO, Cat#298-65701).

Reaction condition. 20 μl soluble starch and 50 μl acetate buffer at pH5.3 were mixed. 30 μl enzyme solution (50 μg enzyme protein/ml) was added to a final volume of 100 μl followed by incubation at 37° C. for 15 min.

The glucose concentration was determined by Wako kits. All the work carried out parallelly.

Temperature optimum. To assess the temperature optimum of the *Penicillium oxalicum* glucoamylase the Reaction condition assay described above was performed at 20, 30, 40, 50, 60, 70, 80, 85, 90 and 95° C. The results are shown in table 1.

TABLE 1

| Temperature optimum | | | | | | | | | | |
|---|---|---|---|---|---|---|---|---|---|---|
| | Temperature (° C.) | | | | | | | | | |
| | 20 | 30 | 40 | 50 | 60 | 70 | 80 | 85 | 90 | 95 |
| Relative activity (%) | 63.6 | 71.7 | 86.4 | 99.4 | 94.6 | 100.0 | 92.9 | 92.5 | 82.7 | 82.8 |

From the results it can be seen that the optimal temperature for *Penicillium oxalicum* glucoamylase at the given conditions is between 50° C. and 70° C. and the glucoamylase maintains more than 80% activity at 95° C.

Heat stability. To assess the heat stability of the *Penicillium oxalicum* glucoamylase the Reaction condition assay was modifed in that the the enzyme solution and acetate buffer was preincubated for 15 min at 20, 30, 40, 50, 60, 70, 75, 80, 85, 90 and 95° C. Following the incubation 20 μl of starch was added to the solution and the assay was performed as described above.

The results are shown in table 2.

TABLE 2

| Heat stability | | | | | | | | | | |
|---|---|---|---|---|---|---|---|---|---|---|
| | Temperature (° C.) | | | | | | | | | |
| | 20 | 30 | 40 | 50 | 60 | 70 | 80 | 85 | 90 | 95 |
| Relative activity (%) | 91.0 | 92.9 | 88.1 | 100.0 | 96.9 | 86.0 | 34.8 | 36.0 | 34.2 | 34.8 |

From the results it can be seen that *Penicillium oxalicum* glucoamylase is stable up to 70° C. after preincubation for 15 min in that it maintains more than 80% activity.

pH optimum. To assess the pH optimum of the *Penicillium oxalicum* glucoamylase the Reaction condition assay described above was performed at pH 2.0, 3.0, 3.5, 4.0, 4.5, 5.0, 6.0 7.0, 8.0, 9.0, 10.0 and 11.0. Instead of using the acetate buffer described in the Reaction condition assay the following buffer was used 100 mM Succinic acid, HEPES, CHES, CAPSO, 1 mM $CaCl_2$, 150 mM KCl, 0.01% Triton X-100, pH adjusted to 2.0, 3.0, 3.5, 4.0, 4.5, 5.0, 6.0 7.0, 8.0, 9.0, 10.0 or 11.0 with HCl or NaOH.

The results are shown in table 3.

TABLE 3

| pH optimum | | | | | | | | | | | |
|---|---|---|---|---|---|---|---|---|---|---|---|
| | pH | | | | | | | | | | |
| | 2.0 | 3.0 | 3.5 | 4.0 | 4.5 | 5.0 | 6.0 | 7.0 | 8.0 | 9.0 | 10.0 | 11.0 |
| Relative activity (%) | 71.4 | 78.6 | 77.0 | 91.2 | 84.2 | 100.0 | 55.5 | 66.7 | 30.9 | 17.8 | 15.9 | 16.1 |

From the results it can be seen that *Penicillium oxalicum* glucoamylase at the given conditions has the highest activity at pH 5.0. The *Penicillium oxalicum* glucoamylase is active in a broad pH range in the it maintains more than 50% activity from pH 2 to 7.

pH stability. To assess the heat stability of the *Penicillium oxalicum* glucoamylase the Reaction condition assay was modifed in that the enzyme solution (50 μg/ml) was preincubated for 20 hours in buffers with pH 2.0, 3.0, 3.5, 4.0, 4.5, 5.0, 6.0 7.0, 8.0, 9.0, 10.0 and 11.0. using the buffers described under pH optimum. After preincubation, 20 μl soluble starch to a final volume of 100 μl was added to the solution and the assay was performed as described above.

The results are shown in table 4.

TABLE 4 pH stability

| | pH | | | | | | | | | | | |
|---|---|---|---|---|---|---|---|---|---|---|---|---|
| | 2.0 | 3.0 | 3.5 | 4.0 | 4.5 | 5.0 | 6.0 | 7.0 | 8.0 | 9.0 | 10.0 | 11.0 |
| Relative activity (%) | 17.4 | 98.0 | 98.0 | 103.2 | 100.0 | 93.4 | 71.2 | 90.7 | 58.7 | 17.4 | 17.0 | 17.2 |

From the results it can be seen that *Penicillium oxalicum* glucoamylase is stable from pH 3 to pH 7 after preincubation for 20 hours and it decreases its activity at pH 8.

Example 9

Saccharification Performance of *Penicillium oxalicum* Glucoamylase

The saccharification performance of the *Penicillium oxalicum* glucoamylase was tested at 70° C. with and without the addition of acid alpha-amylase disclosed as Variant JA001 in WO 2005/003311. Saccharification was run under the following conditions: Substrate: DE11 Maltodextrin, approx. 30% DS (w/w) Temperature: 70° C. Initial pH: 4.3 Enzyme dosage: *Penicillium oxalicum* glucoamylase: 0.075 AGU/g DS with and without acid alpha-amylase: 0.05 AFAU/g DS.

As a control, *A. niger* glucoamylase (uniprot: P69328) was used at 60° C. with 0.225 AGU/g DS.

Saccharification

The substrate for saccharification was made by dissolving DE 11 maltodextrin (prepared from common corn) in boiling Milli-Q water and adjusting the dry substance to approximately 30% (w/w). pH was adjusted to 4.3. Five milliliters of substrate were transferred to 15 ml plastic tube and placed in a water bath at 70° C., and then enzymes were added in the concentrations indicated in table 5. Samples were taken periodically and analyzed using HPLC for determination of the carbohydrate composition.

The glucose produced during saccharification is given in table 5. Numbers are % DP1 (glucose) on DS (dry solids). A glucose yield above 95% was obtained after 72 hours using an enzyme dosage of 0.075 AGU/g DS which is corresponding to 0.016 mg enzyme protein/g DS. Since the dosage of *A. niger* glucoamylase was 0.225 AGU/g DS which is corresponding to 0.12 mg enzyme protein/g DS, a significantly lower enzyme dosage on mg enzyme protein of *Penicillium oxalicum* glucoamylase is therefore required in the saccharification process.

TABLE 5

| | *Penicillium oxalicum* glucoamylase (70° C.) | | *A. niger* glucoamylase (60° C.) | |
|---|---|---|---|---|
| Time (hours) | 0.075 AGU + 0.05 AFAU | 0.075 AGU | 0.225 AGU + 0.05 AFAU | 0.225 AGU |
| 24 | 76.9 | 79.1 | 92.3 | 83.9 |
| 46 | 94.2 | 90.9 | 95.6 | 89.7 |
| 70 | 95.8 | 94.7 | 95.6 | 91.9 |

Example 10

Evaluation of *Penicillium oxalicum* Glucoamylase in 80° C. Liquefaction at pH 4.50 and 5.80

This example illustrates that liquefaction and saccharification can be done simultaneously, achieving a mash which can be fermented into ethanol.

Starting Samples. Ground corn and backset were obtained from Corn LP (Iowa, USA) and used for this experiment. Three slurry samples with a target % dry solids of 32.5% were prepared at 160 g scale using 58 g of ground corn, 53 g of tap water, and 48 g of backset. Two of the slurries were adjusted to pH 5.80 and one was adjusted to pH 4.50.

Liquefaction Treatment. All 3 slurries received a Termamyl™ SC (commercially available alpha-amylase from Novozymes A/S, Bagsvaerd, Denmark) dose of 0.1232 KNU-s/g DS (KNU-s/g dry solids). One of the pH 5.80 slurries received a *Penicillium oxalicum* glucoamylase dose of 0.24 AGU/g DS (AGU/g dry solids), whereas the other received nothing (control mash). The pH 4.50 mash also received a *Penicillium oxalicum* glucoamylase dose of 0.24 AGU/g DS. All slurries were incubated at 80° C. for a total of 2 hours in a preheated water bath, with periodic mixing. After incubation, the mashes were immediately cooled on ice to room temperature. The mashes were adjusted to pH 5.0 and urea and penicillin were added to reach final concentrations of 1000 ppm and 3 ppm, respectively.

Fermentations. Prior to adding approximately 5 g of the mash prepared above to each tube, each empty tube was weighed. After adding the mashes to the appropriate tubes, all tubes were weighed again to measure the initial mash weights. *Penicillium oxalicum* glucoamylase was added to the control mash to a dose of 0.24 AGU/g DS. No glucoamylase was added to the tubes containing the other 2 mashes. RED STAR ETHANOL RED™ yeast from LeSaffre Corp. (Wisconsin, USA) was rehydrated in tap water at 32° C. for 30 minutes (5.50 g into 100 mL tap water), and then 100 µl of this suspension was added to each tube using a repeater pipette. Deionized water was also added to each tube to maintain a constant initial % DS. After the glucoamylase (as appropriate), water, and yeast were added to each tube, they were reweighed and then placed into a constant temperature room set at 32° C. for a total of 58 hours. Twice per day the tubes were removed from the room, vortexed to mix, reweighed, and then placed back into the room to continue fermentations.

After 58 hours of fermentation, all tubes were vortexed, reweighed, and then the fermentations were stopped by the addition of 50 µl of 40% $H_2SO_4$ to each tube, followed by thorough vortexing. The tubes were centrifuged at 1500×g for 10 minutes and then the supernatants were syringe-filtered through 0.45 µm nylon filters into labeled HPLC vials. The samples were then analyzed by HPLC for their contents of ethanol.

The results are shown in table 6. It can be seen that *Penicillium oxalicum* glucoamylase boosed the amount of ethanol, especially when used in Liquefaction at pH 4.50.

TABLE 6

| Sample | Ethanol, g/L |
|---|---|
| 0.24 AGU/g DS *Penicillium oxalicum* glucoamylase in Liquefaction, pH 4.50 | 120.36 |
| 0.24 AGU/g DS *Penicillium oxalicum* glucoamylase in Liquefaction, pH 5.80 | 119.21 |
| Control, no *Penicillium oxalicum* glucoamylase in Liquefaction but in fermentation, pH 5.80 | 118.88 |

Example 11

Evalution of *Penicillium oxalicum* Glucoamylase in 85° C. Liquefaction in Dose—Response at pH 4.50

Starting Samples. Ground corn and backset were obtained from Corn LP and used for this experiment. Ten slurry samples with a target % dry solids of 32.5% were prepared at 125 g scale using 45 g of ground corn, 42 g of tap water, and 38 g of backset. Five of the slurries were adjusted to pH 4.50. One of the slurries served as control.

Liquefaction Treatment. All 5 slurries received a Termamyl™ SC dose of 0.1232 KNU-s/g DS. The five slurries at pH 4.50 received the following doses of *Penicillium oxalicum* glucoamylase: 0-0.0048-0.024-0.048-0.24 AGU/g DS. All slurries were incubated at 85° C. for a total of 2 hours in a preheated water bath, with periodic mixing. After incubation, the mashes were immediately cooled on ice to room temperature. The mashes were adjusted to pH 5.0 and urea and penicillin were added to reach final concentrations of 1000 ppm and 3 ppm, respectively.

Fermentations. Prior to adding approximately 5 g of the mash to each tube, each empty tube was weighed. After adding the mashes to the appropriate tubes, all tubes were weighed again to measure the initial mash weights. *Talaromyces emersonii* glucoamylase was added to each tube to a concentration of 0.50 AGU/g DS. RED STAR ETHANOL RED™ yeast from LeSaffre Corp. was rehydrated in tap water at 32° C. for 30 minutes (5.50 g into 100 mLs tap water), and then 100 µL of this suspension was added to each tube using a repeater pipette. Deionized water was also added to each tube to maintain a constant initial % DS. After the *Talaromyces emersonii* glucoamylase, water, and yeast were added to each tube, they were reweighed and then placed into a constant temperature room set at 32° C. for a total of 54 hours. Twice per day the tubes were removed from the room, vortexed to mix, reweighed, and then placed back into the room to continue fermentations.

After 54 hours of fermentation, all tubes were vortexed, reweighed, and then the fermentations were stopped by the addition of 50 µl of 40% $H_2SO_4$ to each tube, followed by thorough vortexing. The tubes were centrifuged at 1500×g for 10 minutes and then the supernatants were syringe-filtered through 0.45 µm nylon filters into labeled HPLC vials. The samples were then analyzed by HPLC for their contents of ethanol.

Results are shown in table 7. It can be seen that ethanol produced from ground corn and backset is improved by *Penicillium oxalicum* glucoamylase in Liquefaction in dose-response.

TABLE 7

| Sample | Ethanol, g/L |
|---|---|
| Control, no *Penicillium oxalicum* glucoamylase in Liquefaction | 128.33 |
| 0.0048 AGU/g DS *Penicillium oxalicum* glucoamylase in Liquefaction | 128.57 |
| 0.024 AGU/g DS *Penicillium oxalicum* glucoamylase in Liquefaction | 128.75 |
| 0.048 AGU/g DS *Penicillium oxalicum* glucoamylase in Liquefaction | 130.51 |
| 0.24 AGU/g DS *Penicillium oxalicum* glucoamylase in Liquefaction | 132.27 |

Example 12

Futher Evaluation of *Penicillium oxalicum* Glucoamylase in Liquefaction at pH 4.5 and 85° C.

Slurry Sample. A slurry sample prepared in the pilot plant at the National Corn to Ethanol Research Center (NCERC) during May of 2008 was used as a starting material for this study. The sample was prepared using whole ground corn (no backset) at a target % dry solids of 32.0%. It was liquefied at pH 5.80, 85° C. for 30 minutes using 0.0492 KNU-s/g DS of Termamyl™ SC.

Liquefaction Treatment. Six different fully-liquefied corn mashes were prepared using the NCERC slurry sample described above as starting material. Briefly, approximately 110 g of the slurry mash was weighed into 5 separate 250 ml Nalgene bottles. The slurry mash samples were adjusted to pH 4.50 using 40% $H_2SO_4$. Aliquots of *Penicillium oxalicum* glucoamylase were then added to each mash to reach final enzyme doses of 0-0.0048-0.024-0.048-0.096-0.24 AGU/g DS. 0.0740 KNU-s/g DS of Termamyl™ SC was also added to each mash. The mashes were incubated at 85° C. for an additional 1.5 hours in a preheated water bath, with periodic mixing. After incubation, the mashes were immediately cooled on ice to room temperature. The mashes were adjusted to pH 5.0 using 10% NaOH and urea and penicillin were added to reach final concentrations of 1000 ppm and 3 ppm, respectively. Small samples of each mash were taken for HPLC analysis to measure the amount of the available starch that was converted to glucose during liquefaction. For these calculations, the percentage of the starting ground corn that was starch was assumed to be 30.0%.

The results are shown in table 8. It can be seen that the percentage of starch converted to glucose in liquefaction was enhanced by the addition of *Penicillium oxalicum* glucoamylase in the liquefaction treatment.

TABLE 8

| Mash | Glucose (g/L) | % Starch to Glucose |
|---|---|---|
| Control, no *Penicillium oxalicum* glucoamylase in Liquefaction | 8.4 | 3.6% |
| 0.0048 AGU/g DS *Penicillium oxalicum* glucoamylase in Liquefaction | 9.2 | 4.0% |
| 0.024 AGU/g DS *Penicillium oxalicum* glucoamylase in Liquefaction | 22.9 | 9.9% |
| 0.048 AGU/g DS *Penicillium oxalicum* glucoamylase in Liquefaction | 39.4 | 17.1% |
| 0.096 AGU/g DS *Penicillium oxalicum* glucoamylase in Liquefaction | 71.9 | 31.1% |
| 0.24 AGU/g DS *Penicillium oxalicum* glucoamylase in Liquefaction | 123.7 | 53.5% |

Fermentations. Prior to adding approximately 5 g of the mash generated in the liquefication treatment above to each tube, each empty tube was weighed. After adding the mashes to the appropriate tubes, all tubes were weighed again to measure the initial mash weights. *Talaromyces emersonii* glucoamylase stock solution was then added to each of the tubes to an initial dose of 0.50 AGU/g DS. RED STAR ETHANOL RED™ yeast from LeSaffre Corp. was rehydrated in tap water at 32° C. for 30 minutes (5.50 g into 100 mLs tap water), and then 100 μl of this yeast suspension was added to each tube using a repeater pipette. Deionized water was also added to each tube to maintain a constant initial % DS. After the *Talaromyces emersonii* glucoamylase, water, and yeast were added to each tube, they were reweighed and then placed into a constant temperature room set at 32° C. for a total of 54 hours. Twice per day the tubes were removed from the room, vortexed to mix, reweighed, and then placed back into the room to continue fermentations.

After 54 hours of fermentation, all tubes were vortexed, reweighed, and then the fermentations were stopped by the addition of 50 μl of 40% $H_2SO_4$ to each tube, followed by thorough vortexing. The tubes were centrifuged at 1500×g for 10 minutes and then the supernatants were syringe-filtered through 0.45 μm nylon filters into labeled HPLC vials. The samples were then analyzed by HPLC for their contents of ethanol.

The results are shown in table 9. It can be seen that *Penicillium oxalicum* glucoamylase enhanced ethanol production when used in liquefaction at pH 4.5.

TABLE 9

| Treatment | Ethanol, g/L |
| --- | --- |
| Control, no *Penicillium oxalicum* glucoamylase in Liquefaction | 110.14 |
| 0.0048 AGU/g DS *Penicillium oxalicum* glucoamylase in Liquefaction | 110.75 |
| 0.024 AGU/g DS *Penicillium oxalicum* glucoamylase in Liquefaction | 111.70 |
| 0.048 AGU/g DS *Penicillium oxalicum* glucoamylase in Liquefaction | 112.25 |
| 0.096 AGU/g DS *Penicillium oxalicum* glucoamylase in Liquefaction | 112.70 |
| 0.24 AGU/g DS *Penicillium oxalicum* glucoamylase in Liquefaction | 113.31 |

Example 13

Evaluation of *Penicillium oxalicum* Glucoamylase in Pre-Saccharification at pH 5.0 and 70° C.

This example describes an ethanol production process where *Penicillium oxalicum* glucoamylase is used in a pre-saccharification process followed by a fermentation process without using additional glucoamylase. This process is compared with a traditional ethanol production process where the liquefication process is followed by a SSF process using a non-heatstable glucoamylase.

Slurry Sample. A slurry sample prepared in the pilot plant at the National Corn to Ethanol Research Center (NCERC) during May of 2008 was used as a starting material for this study. The sample was prepared using whole ground corn (no backset) at a target % dry solids of 32.0%. It was liquefied at pH 5.80, 85° C. for 30 minutes using 0.0246 KNU-s/g DS of Termamyl™ SC.

Liquefaction Treatment. One fully-liquefied corn mash was prepared using the NCERC slurry sample described above as starting material. Briefly, approximately 400 g of the slurry mash was weighed into a 1 L Nalgene bottle; the slurry mash sample was adjusted to pH 5.80 using 40% $H_2SO_4$. 0.0740 KNU-s/g DS of Termamyl™ SC was added to th mash which was then incubated at 85° C. for an additional 1.5 hours in a preheated water bath, with periodic mixing.

pre-saccharification. After incubation, the mash was aliquoted into two 100 mL Nalgene bottles, cooled down to 70° C. in a water bath and aliquots of *Penicillium oxalicum* glucoamylase were added to each mash to reach final enzyme of 0 and 0.24 AGU/gDS. The mashes were incubated at 70° C. for an additional 2 hours in the water bath, with periodic mixing. After incubation, the mashes were immediately cooled to room temperature. The mashes were adjusted to pH 5.0 using 10% NaOH and urea and penicillin were added to reach final concentrations of 1000 ppm and 3 ppm, respectively. Small samples of each mash were taken for HPLC analysis.

The results are shown in table 10. It can be seen that the percentage of starch converted into glucose in pre-saccharification was enhanced by the addition of *Penicillium oxalicum* glucoamylase.

TABLE 10

| Mash | Glucose (g/L) | % Starch to Glucose |
| --- | --- | --- |
| Control, no *Penicillium oxalicum* glucoamylase in pre-saccharification | 8.43 | 3.6% |
| 0.24 AGU/g DS *Penicillium oxalicum* glucoamylase in pre-saccharification | 136.91 | 58.5% |

Fermentations. Prior to adding approximately 5 g of mash to each tube, each empty tube was weighed. After adding the mashes to the appropriate tubes, all tubes were weighed again to measure the initial mash weights. *Talaromyces emersonii* glucoamylase stock solution was then added to the control tube to an initial dose of 0.50 AGU/g DS whereas no additional glucoamylase was added to the sample which received *Penicillium oxalicum* glucoamylase in the pre-saccrification.

RED STAR ETHANOL RED™ yeast from LeSaffre Corp. was rehydrated in tap water at 32° C. for 30 minutes (5.50 g into 100 mLs tap water), and then 100 μl of this suspension was added to each tube using a repeater pipette. Deionized water was also added to each tube to maintain a constant initial % DS. After the *Talaromyces emersonii* glucoamylase, water, and yeast were added to each tube, they were reweighed and then placed into a constant temperature room set at 32° C. for a total of 54 hours. Twice per day the tubes were removed from the room, vortexed to mix, reweighed, and then placed back into the room to continue fermentations.

After 54 hours of fermentation, all tubes were vortexed, reweighed, and then the fermentations were stopped by the addition of 50 μl of 40% $H_2SO_4$ to each tube, followed by thorough vortexing to mix. The tubes were centrifuged at 1500×g for 10 minutes and then the supernatants were syringe-filtered through 0.45 μm nylon filters into labeled HPLC vials. The samples were then analyzed by HPLC for their contents of ethanol.

The results are shown in table 11. It can be seen that *Penicillium oxalicum* glucoamylase when used in the pre-saccrificartion step at pH 5.80 at 70° C. produced an amount of ethanol equivalent to the amount of ethanol produced by the conventional process (control). This a very good result considering that only half the amount of *Penicillium oxalicum* glucoamylase activity was used compared to the *Talaromyces emersonii* glucoamylase activity (0.5 AGU/g DS).

TABLE 11

| Treatment | Ethanol, g/L |
|---|---|
| Control, no *Penicillium oxalicum* glucoamylase in pre-saccharification, but 0.5 AGU/g DS *Talaromyces emersonii* glucoamylase in the fermentation | 110.14 |
| 0.24 AGU/g DS *Penicillium oxalicum* glucoamylase in pre-saccharification | 110.86 |

DEPOSIT OF BIOLOGICAL MATERIAL

The following biological material has been deposited under the terms of the Budapest Treaty with the Deutsche Sammlung von Mikroorganismen and Zellkulturen GmbH (DSMZ), Mascheroder Weg 1 B, D-38124 Braunschweig, Germany and given the following accession number:

Deposit *E. coli* Strain NN059173 with plasmid comprising sequence *Penicillium oxalicum* glucoamylase Accession Number DSM 23123    Date of Deposit Nov. 23, 2009

The strain has been deposited under conditions that assure that access to the culture will be available during the pendency of this patent application to one determined by foreign patent laws to be entitled thereto. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and describederein will become apparent to those skilled in the art from the foregoing description. Such modifications are also intended to fall within the scope of the appended claims. In the case of conflict, the present disclosure including definitions will control.

What is claimed is:

1. A nucleic acid construct comprising a polynucleotide comprising a nucleic acid sequence that encodes a *Penicillium* polypeptide having glucoamylase activity and at least 75% sequence identity to the amino acids 22 to 616 of SEQ ID NO: 2, and is operably linked to one or more heterologous control sequences that direct the production of the polypeptide in an expression host.

2. A recombinant expression vector comprising the nucleic acid construct of claim 1.

3. A recombinant host cell comprising the nucleic acid construct of claim 1.

4. The recombinant host cell of claim 3, which is a fungal host cell.

5. The recombinant host cell of claim 3, which is a yeast host cell.

6. The recombinant host cell of claim 3, which is a yeast host cell selected from the group consisting of a *Candida* cell, *Hansenula* cell, *Kluyveromyces* cell, *Pichia* cell, *Saccharomyces* cell, *Schizosaccharomyces* cell, and a *Yarrowia* cell.

7. The recombinant host cell of claim 3, which is a yeast host cell selected from the group consisting of a *Saccharomyces diastaticus* cell, a *Saccharomyces douglasii* cell, a *Saccharomyces kluyveri* cell, a *Saccharomyces norbensis* cell, and a *Saccharomyces oviformis* cell.

8. The recombinant host cell of claim 3, which is a *Kluyveromyces lactic* cell or a *Yarrowia lipolytica* call.

9. The recombinant host cell of claim 3, which is a *Saccharomyces cerevisiae* cell.

10. A method of producing a *Penicillium* polypeptide having glucoamylase activity and at least 75% sequence identity to amino acids 22 to 616 of SEQ ID NO: 2, comprising:
    (a) cultivating a host cell comprising a nucleic acid construct comprising a polynucleotide encoding the polypeptide under conditions conducive for production of the polypeptide; and
    (b) recovering the polypeptide.

11. A composition comprising a *Penicillium* polypeptide having at least 75% sequence identity to amino acids 22 to 616 of SEQ ID NO: 2, and an alpha-amylase, wherein the polypeptide has glucoamylase activity and the alpha-amylase has alpha-amylase activity.

12. A process for producing a liquefaction, saccharification and/or fermentation product from starch-containing material comprising treating starch-containing material with a *Penicillium* polypeptide having glucoamylase activity and at least 75% sequence identity to amino acids 22 to 616 of SEQ ID NO: 2.

13. The process of claim 12, wherein an alpha-amylase is added.

14. The process of claim 12, wherein the starch-containing material is corn.

15. The process of claim 12, wherein the treating is carried out at a temperature between 40° C. and 100° C. and/or at a pH between 2.0 and 7.0.

16. A process of producing a saccharified material, comprising saccharifying a starch with a *Penicillium* polypeptide having glucoamylase activity and at least 75% sequence identity to amino acids 22 to 616 of SEQ ID NO: 2.

17. A process of producing a fermentation product, comprising
    (a) liquefying a starch material to produce a liquefied starch material;
    (b) saccharifying the liquefied starch material with a *Penicillium* polypeptide having at least 75% sequence identity to amino acids 22 to 616 of SEQ ID NO: 2 to produce a sugar; and
    (c) fermenting the sugar to produce the fermentation product.

18. The process of claim 17, further comprising recovering the fermentation product.

19. The process of claim 17, wherein the fermentation product is ethanol.

20. The process of claim 17, wherein the starch-containing material is corn.

21. The nucleic acid construct of claim 1, wherein the *Penicillium* polypeptide is selected from the group consisting of *P. oxalicum*, *P. purpurogenum*, *P. thomii*, and *P. funiculosum*.

22. The recombinant expression vector of claim 2, wherein the *Penicillium* polypeptide is selected from the group consisting of *P. oxalicum*, *P. purpurogenum*, *P. thomii*, and *P. funiculosum*.

23. The recombinant host cell of claim 3, wherein the *Penicillium* polypeptide is selected from the group consisting of *P. oxalicum*, *P. purpurogenum*, *P. thomii*, and *P. funiculosum*.

24. The method of claim 10, wherein the *Penicillium* polypeptide is selected from the group consisting of *P. oxalicum*, *P. purpurogenum*, *P. thomii*, and *P. funiculosum*.

25. The composition of claim 11, wherein the *Penicillium* polypeptide is selected from the group consisting of *P. oxalicum*, *P. purpurogenum*, *P. thomii*, and *P. funiculosum*.

26. The process of claim 12, wherein the *Penicillium* polypeptide is selected from the group consisting of *P. oxalicum, P. purpurogenum, P. thomii,* and *P. funiculosum.*

27. The process of claim 16, wherein the *Penicillium* polypeptide is selected from the group consisting of *P. oxalicum, P. purpurogenum, P. thomii,* and *P. funiculosum.*

28. The process of claim 17, wherein the *Penicillium* polypeptide is selected from the group consisting of *P. oxalicum, P. purpurogenum, P. thomii,* and *P. funiculosum.*

\* \* \* \* \*